(12) United States Patent
Packirisamy et al.

(10) Patent No.: US 10,345,234 B2
(45) Date of Patent: Jul. 9, 2019

(54) METHODS FOR FABRICATING MORPHOLOGICALLY TRANSFORMED NANO-STRUCTURES (MTNS) AND TUNABLE NANOCOMPOSITE POLYMER MATERIALS, AND DEVICES USING SUCH MATERIALS

(71) Applicant: CONCORDIA UNIVERSITY, Montreal (CA)

(72) Inventors: Muthukumaran Packirisamy, Pierrefonds (CA); Jayan Ozhikandathil, Montreal (CA); Ajit Khosla, Yamagata-Ken (JP)

(73) Assignee: Concordia University, Montreal (CA)

( * ) Notice: Subject to any disclaimer, the term of this patent is extended or adjusted under 35 U.S.C. 154(b) by 507 days.

(21) Appl. No.: 14/776,833

(22) PCT Filed: Mar. 17, 2014

(86) PCT No.: PCT/CA2014/050281
§ 371 (c)(1),
(2) Date: Sep. 15, 2015

(87) PCT Pub. No.: WO2014/139031
PCT Pub. Date: Sep. 18, 2014

(65) Prior Publication Data
US 2016/0033403 A1      Feb. 4, 2016

Related U.S. Application Data

(60) Provisional application No. 61/793,474, filed on Mar. 15, 2013.

(51) Int. Cl.
*B01L 3/00* (2006.01)
*B22F 1/00* (2006.01)
(Continued)

(52) U.S. Cl.
CPC ...... *G01N 21/554* (2013.01); *B01L 3/502715* (2013.01); *B22F 1/0062* (2013.01);
(Continued)

(58) Field of Classification Search
CPC ................. G01N 21/554; G01N 21/33; G01N 33/54373; B01L 3/502715; B01L 2200/10;
(Continued)

(56) References Cited

U.S. PATENT DOCUMENTS 9,164,034 B2    10/2015 Rubinstein et al.

OTHER PUBLICATIONS

Ozhikandathil, Jayan, Simona Badilescu, and Muthukumaran Packirisamy. "Synthesis and characterization of silver—PDMS nanocomposite for the biosensing applications." Proceedings of SPIE. 2011.*

(Continued)

*Primary Examiner* — Robert J Eom
(74) *Attorney, Agent, or Firm* — Stinson LLP

(57) ABSTRACT

In order to implement a microfluidics sensor having higher efficiency, Applicants have developed a method of formation of nano-structures having various shapes and sizes onto materials such as polymers, glass and silicon, which are compatible with the microfabrication processes. The adhesion of the nano-structures and feasibility to tune their properties (optical, electrical and mechanical) are two prime concerns when they are adopted for microfluidics devices.

8 Claims, 24 Drawing Sheets

(51) Int. Cl.

| | |
|---|---|
| *B22F 9/24* | (2006.01) |
| *C08J 5/00* | (2006.01) |
| *H01B 1/22* | (2006.01) |
| *B82Y 30/00* | (2011.01) |
| *B82Y 40/00* | (2011.01) |
| *G01N 21/33* | (2006.01) |
| *G01N 21/552* | (2014.01) |
| *G01N 33/543* | (2006.01) |

(52) U.S. Cl.
CPC ............... *B22F 9/24* (2013.01); *C08J 5/005* (2013.01); *G01N 21/33* (2013.01); *G01N 33/54373* (2013.01); *H01B 1/22* (2013.01); *B01L 2200/10* (2013.01); *B01L 2300/0654* (2013.01); *B01L 2300/0809* (2013.01); *B01L 2300/16* (2013.01); *B82Y 30/00* (2013.01); *B82Y 40/00* (2013.01)

(58) Field of Classification Search
CPC ......... B01L 2300/16; B01L 2300/0809; B01L 2300/0654; B22F 1/0062; B22F 9/24; C08J 5/005; H01B 1/22; B82Y 30/00; B82Y 40/00
See application file for complete search history.

(56) References Cited

OTHER PUBLICATIONS

Khosla, Ajit. Micropatternable multifunctional nanocomposite polymers for flexible soft MEMS applications. Diss. Applied Science: School of Engineering Science, 2011.*
J. Ozhikandathil, S. Badilescu and M. Packirisamy, "Gold nanoisland structures integrated in a lab-on-a-chip for plasmonic detection of bovine growth hormone," J. Biomed. Opt., vol. 17, pp. 077001, Jul. 2012.
N. Nath and A. Chilkoti, "Label-free biosensing by surface plasmon resonance of nanoparticles on glass: optimization of nanoparticle size," Anal. Chem., vol. 76, pp. 5370-5378, Sep. 15, 2004.
N. Nath and A. Chilkoti, "Label free calorimetric biosensing using nanoparticles," J. Fluorescence, vol. 14, pp. 377-389, Jul. 2004.
J. Ye, K. Bonroy, D. Nelis, F. Frederix, J. D'Haen, G. Maes and G. Borghs, "Enhanced localized surface plasmon resonance sensing on three-dimensional gold nanoparticles assemblies," Colloids and Surfaces Physicochem. Eng. Aspects, vol. 321, pp. 313-317, Jan. 2008.
A. L. Weikel, S. D. Conklin and J. N. Richardson, "A multiple reflection attenuated total reflectance sensor incorporating a glass-indium tin oxide surface modified via direct attachment or film encapsulation of colloidal gold nanoparticles," Sensors Actuators B: Chem., vol. 110, pp. 112-119, Feb. 2005.
F. Frederix, J. M. Friedt, K. H. Choi, W. Laureyn, A. Campitelli, D. Mondelaers, G. Maes and G. Borghs, "Biosensing based on light absorption of nanoscaled gold and silver particles," Anal. Chem., vol. 75, pp. 6894-6900, Dec. 15, 2003.
J. C. Hulteen, D. A. Treichel, M. T. Smith, M. L. Duval, T. R. Jensen and R. P. Van Duyne, "Nanosphere lithography: size-tunable silver nanoparticle and surface cluster arrays," The Journal of Physical Chemistry B, vol. 103, pp. 3854-3863, Apr. 29, 1999.
F. Fida, L. Varin, S. Badilescu, M. Kahrizi and V. V. Truong, "Gold Nanoparticle Ring and Hole Structures for Sensing Proteins and Antigen—Antibody Interactions," Plasmonics, vol. 4, pp. 201-207, May 21, 2009.
K. Fujiwara, H. Watarai, H. Itoh, E. Nakahama and N. Ogawa, "Measurement of antibody binding to protein immobilized on gold nanoparticles by localized surface plasmon spectroscopy," Analytical and Bioanalytical Chemistry, vol. 386, pp. 639-644, Jul. 6, 2006.
L. Guo, G. Chen and D. H. Kim, "Three-dimensionally assembled gold nanostructures for plasmonic biosensors," Anal. Chem., vol. 82, pp. 5147-5153, May 14, 2010.
X. Wang, K. Naka, M. Zhu, H. Kuroda, H. Itoh and Y. Chujo, "Self-organized multilayer films and porous nanocomposites of gold nanoparticles with octa (3-aminopropyl) octasilsesquioxane," Journal of Inorganic and Organometallic Polymers and Materials, vol. 17, pp. 447-457, Jun. 2007.
F. Toderas, M. Baia, L. Baia and S. Astilean, "Controlling gold nanoparticle assemblies for efficient surface-enhanced Raman scattering and localized surface plasmon resonance sensors," Nanotechnology, vol. 18, pp. 255702, May 29, 2007.
W. Cheng, S. Dong and E. Wang, "Two-and three-dimensional Au nanoparticle/CoTMPyP self-assembled nanotructured materials: film structure, tunable electrocatalytic activity, and plasmonic properties," The Journal of Physical Chemistry B, vol. 108, pp. 19146-19154, Nov. 17, 2004.
S. Szunerits, M. R. Das and R. Boukherroub, "Short-and long-range sensing on gold nanostructures, deposited on glass, coated with silicon oxide films of different thicknesses," The Journal of Physical Chemistry C, vol. 112, pp. 8239-8243, May 7, 2008.
S. Szunerits, V. G. Praig, M. Manesse and R. Boukherroub, "Gold island films on indium tin oxide for localized surface plasmon sensing," Nanotechnology, vol. 19, pp. 195712, Apr. 8, 2008.
W.Rechberger, A. Hohenau, A. Leitner, J Krenn, B. Lamprecht and F. Aussengg, "Optical Properties of two interacting gold nanoparticles," Opt. Commun., vol. 220, pp. 137-141, 2003.
"International Preliminary Report on Patentability Issued in PCT Application No. PCT/CA2014/050281", dated Sep. 15, 2015, 6 Pages.

* cited by examiner

METHODS FOR FABRICATING MORPHOLOGICALLY TRANSFORMED NANO-STRUCTURES (MTNS) AND TUNABLE NANOCOMPOSITE POLYMER MATERIALS, AND DEVICES USING SUCH MATERIALS

CLAIM OF PRIORITY

This application claims the benefit of and is a National Phase Entry of International Application Number PCT/CA2014/050281 filed Mar. 17, 2014, and claims the benefit of priority from U.S. Provisional Patent Application No. 61/793,474 filed on Mar. 15, 2013, which are both incorporated herein in their entirety.

FIELD OF THE INVENTION

The invention relates to morphologically transformed nano-structures (MTNS) and tunable nanocomposite polymer materials.

BACKGROUND OF THE INVENTION

Optical absorption spectrum in the ultra-violet and visible (UV-Vis) range of metallic nano-structures has been used as a label-free (i.e. without tagging with particles that emit light at different wavelength than the wavelength they are excited with, such as, for example fluorophores) technique for the detection of binding events in real time. A sensing mechanism is based on for example, a change in the position and/or the intensity of the spectrum or upon a change of refractive index of the medium surrounding the sensing mechanism. The refractive index of the surrounding medium has a strong influence on the absorption bands of nano-structures in the visible and near visible regions, thereby monitoring the absorption bands is highly useful for plasmonic detection of biomolecules.

A main fabrication process step of nano-biosensors is the immobilization of nano-structures on a substrate. Several techniques such as nanosphere lithography (NSL), vapor deposition, thermal evaporation and electrochemical deposition are reported for the immobilization of nanoparticles on various substrates. Using NSL, ordered nano-structures can be deposited with the help of self assembled polystyrene spheres and vacuum deposition. A widely reported method of fabrication of nano-island structures is the deposition of a thin film of gold on a substrate by vacuum deposition and annealing to yield nano-island morphology.

Presently, there is a huge demand for microfluidic devices as they are capable of performing bio-detection and drug delivery applications using small amounts (nano-liters) of bio-liquids and reagents.

Most chip-based bio-assays are based on two-dimensional (2D) chips, that is, a gold monolayer on glass having a low density of nanoparticles that are deposited on a sensing substrate and the immunoassays are carried out. Various deposition methods explained above have been reported for the fabrication of 2D chips, but these are not generally compatible with the fabrication of micro-devices. Hence new fabrication methods are essential for the development of lab-on-a-chip (LOC) devices. Integration of nano-structures in microfluidics chips is an emerging trend for the developments of high throughputs LOC devices.

SUMMARY OF THE INVENTION

In order to implement a microfluidics sensor having higher efficiency, a method of formation of nano-structures having various shapes and sizes onto materials such as polymers, glass and silicon, which are compatible with the microfabrication processes is provided. The adhesion of the nano-structures and feasibility to tune their properties (optical, electrical and mechanical) are two prime concerns when they are adopted for microfluidics devices.

In some embodiments of the present invention, in-situ synthesis of silver nano-structures formed on a substrate inside a microfluidic device integrated with an optical assembly directly with the microfluidic device, may result in a portable and low-cost device.

In some embodiments, a nanocomposite polymer is fabricated based on a partial reduction of metal salts, which balances the reduction of nanoparticles and the crosslinking of the polymer. In some embodiments, the partial reduction of metal salts is achieved by a controlled addition of curing agent and solvents of metal salts.

According to an aspect of the invention, there is provided a method of fabrication of nanoparticle reinforced polymer comprising: performing a partial and controlled reduction of metal salts to metal nanoparticles by using a crosslinking or curing agent during the preparation process of the polymer; and adding electrically conductive nanoparticles to the polymer during the preparation process.

In some embodiments performing a partial and controlled reduction of metal salts comprises controlling the reduction by varying the concentration of the metal salts and the crosslinking agent.

In some embodiments performing a partial and controlled reduction of metal salts to nanoparticles comprises: tuning at least one of optical, electrical, mechanical, thermal and chemical properties of the polymer for various applications by controlling the percentage weight (wt %) of the nanoparticles in the polymer by adjusting an amount of crosslinking agent and a concentration of the metal salts during preparation of polymer.

In some embodiments the method further comprises using the nanoparticle reinforced polymer for fabricating microdevices and nanodevices having nanostructures with enhanced material properties.

In some embodiments subsequent to adding electrically conductive nanoparticles to the polymer the method further comprises mechanically stimulating the polymer to mix the electrically conductive nanoparticles of same or different shapes and sizes uniformly in the polymer.

In some embodiments the tuned optical properties and surface properties of the nanoparticle reinforced polymer aid in immobilizing bio/chemical test material for easier detection by virtue of uniform distribution of nanoparticles on a surface of the nanoparticle reinforced polymer.

In some embodiments the polymer is one of: Polydimethylsiloxane (PDMS); Poly(methyl methacrylate) (PMMA); Polyurethane (PUR and PU); Polystyrene (PS); Ethylene Copolymer; Cyclo Olefinecopolymer; Cyclic Olefin Polymer (COC); Ethylene-norbomene Copolymer; Low Density Polyethylene (LDPE); High Density Polyethylene (HDPE); Polypropylene (PP); Polyvinyl Chloride (PVC); Nylon; Teflon (Polytetrafluoroethylene); Thermoplastic polyurethanes (TPU); ethylenedioxythiophene silicones; Polyethylene poly(styrenesulfonate); polycarbazoles; polyindoles; and polyazepines.

According to another aspect of the invention, there is provided a nanocomposite material fabricated by a partial and controlled reduction of metal salts to metallic nanoparticles by using a crosslinking agent and the addition of electrically conductive nanoparticles during the preparation process of the polymer.

In some embodiments the nanocomposite is fabricated using the nanoparticle material for fabricating microdevices and nanodevices having nanostructures with enhanced material properties.

In some embodiments the nanocomposite is suitable for various sensing applications including, biological, thermal and mechanical sensing.

In some embodiments the nanocomposite is used for fabricating flexible micro or nano electronics or electrical circuits.

In some embodiments the microdevices and nanodevices are one or more of: microelectronic sensors; electronic sensors; ECG, EKG, bio-potential sensors; heating pads with ribbon cables; strain gauges; tunable antennas; flexible electronics; tactile sensors; Microelectromechanical System (MEMS) devices; and interdigitated electrodes.

In some embodiments the nanocomposite has enhanced mechanical properties that can be used to form part of a component that is flexible.

In some embodiments the flexible component is one or more of: a flexible antenna, a flexible signal or electrical routing component, or a flexible heating component.

In some embodiments the polymer is one of: Polydimethylsiloxane (PDMS); Poly(methyl methacrylate) (PMMA); Polyurethane (PUR and PU); Polystyrene (PS); Ethylene Copolymer; Cyclo Olefinecopolymer; Cyclic Olefin Polymer (COC); Ethylene-norbomene Copolymer; Low Density Polyethylene (LDPE); High Density Polyethylene (HDPE); Polypropylene (PP); Polyvinyl Chloride (PVC); Nylon; Teflon (Polytetrafluoroethylene); Thermoplastic polyurethanes (TPU); ethylenedioxythiophene silicones; Polyethylene poly(styrenesulfonate); polycarbazoles; polyindoles; and polyazepines.

In some embodiments the nanocomposite is patternable.

In some embodiments the nanocomposite can be used in nano-microscale printing on various dielectric and non-dielectric substrates.

In some embodiments the dielectric and non-dielectric substrates include fabrics, plastics and glass.

According to an aspect of the invention, there is provided a method of fabricating a device for bio-sensing comprising: integrating metallic nanofeatures onto a substrate; and annealing the substrate to perform morphology tuning of the nanofeatures.

In some embodiments, integrating metallic nanofeatures on the substrate comprises using aqueous silver nitrate to synthesize silver nanofeatures on the substrate.

In some embodiments, annealing the substrate comprises heating the substrate to a temperature below the melting temperature of the metallic nanofeature material.

In some embodiments, annealing the substrate comprises heating the substrate to between 250° C. and 450° C.

In some embodiments, annealing the substrate comprises heating the substrate to between 300° C. and 400° C.

In some embodiments, annealing the substrate comprises heating the PDMS substrate to between 340° C. and 370° C.

In some embodiments, integrating the metallic nanofeatures comprises depositing the metal on a substrate that is at least one of: Polydimethylsiloxane (PDMS); glass; silicon; or a polymer.

According to another aspect of the invention, there is provided a method comprising: optimizing the annealing of metallic nano-clusters for use in the formation of morphologically transformed nano-structures (MTNS) suitable for the bio-sensing.

In some embodiments, optimizing annealing the metallic nano-clusters comprises: selecting a temperature for annealing metallic nano-clusters that is below the melting temperature of the metallic nano-cluster material.

In some embodiments, optimizing annealing the metallic nano-clusters comprises: selecting a temperature for annealing metallic nano-clusters on a substrate between 250° C. and 450° C.

In some embodiments, optimizing annealing the metallic nano-clusters comprises: selecting a temperature for annealing metallic nano-clusters on a substrate between 300° C. and 400° C.

In some embodiments, optimizing annealing the metallic nano-clusters comprises: selecting a temperature for annealing metallic nano-clusters on a substrate between 340° C. and 370° C.

According to a further aspect of the invention, there is provided a device for use in bio-sensing, the device comprising: high sensitivity morphologically transformed nano-structures (MTNS) fabricated by morphology tuning of metallic nano-clusters integrated on a substrate.

In some embodiments, the metallic nano-cluster is integrated on the substrate using an in-situ synthesis process of an aqueous metal solution interacting with the substrate.

In some embodiments, using an in-situ synthesis process of an aqueous metal solution interacting with the substrate comprises using an in-situ synthesis process of aqueous silver nitrate interacting with the substrate.

In some embodiments, morphology tuning of the metallic nano-clusters is performed by heating the substrate to a temperature that is below the melting temperature of the metallic nano-cluster material.

In some embodiments, morphology tuning of the metallic nano-clusters is performed by heating the substrate to a temperature that is between 250° C. and 450° C.

In some embodiments, morphology tuning of the metallic nano-clusters is performed by heating the substrate to a temperature that is between 300° C. and 400° C.

In some embodiments, morphology tuning of the metallic nano-clusters is performed by heating the substrate to a temperature that is between 340° C. and 370° C.

In some embodiments, the MTNS are formed on a sensing platform within a microfluidic platform.

In some embodiments, the microfluidic platform comprises: a sensing chamber for containing bio-reagents for testing within which the sensing platform is located; one or more micro-channels fluidly connecting a first fluid reservoir for supplying bio-reagents to the sensing chamber; one or more micro-channels fluidly connecting the sensing chamber to a second fluid reservoir for removing bio-reagents; and at least one optical waveguide proximate the sensing chamber to supply a radiation source into the sensing chamber and detect radiation emanating from the sensing chamber.

In some embodiments, the microfluidic platform is comprised of at least two portions, a first portion being the substrate with the sensing chamber, reservoirs, micro-channels and optical waveguides and a second portion being a cover to enclose at least the sensing chamber, reservoirs, micro-channels.

In some embodiments, the first and second portions are bonded together.

In some embodiments, the microfluidic platform is fabricated from one or more of: glass; PDMS; silicon; transparent polymers; metal; and ceramic.

In some embodiments, the substrate on which the metallic nanoclusters are formed is fabricated from one or more of: glass; PDMS; transparent polymers; silicon and composites thereof.

According to yet another aspect of the invention there is provided a system comprising: a device as described above or detailed below; at least one pump for supply and extracting reagents to the device; a radiation source to supply light to the device; and a radiation detector to detect radiation emanating from the device.

According to yet another aspect of the invention, there is provided a method for performing bio-sensing comprising: introducing a linker to functionalize a surface of morphologically transformed nano-structures (MTNS) in order to bind a desired bio-molecule; introducing an antibody of a desired antigen and recording the absorption spectrum with a UV-Vis measurement device; introducing the antigen to be detected and recording the absorption spectrum with the UV-Vis measurement device; and analyzing the change in the absorption spectrum, thereby quantifying the degree of bio molecular interaction between the antibody and the antigen.

In some embodiments, the method further comprises: depositing a metal on a substrate to integrate metallic nanofeatures into the substrate; and annealing the substrate to perform morphology tuning of the metallic nanofeatures thereby generating morphologically transformed nanostructures (MTNS).

According to yet a further aspect of the invention there is provided an integration of MTNS with structures that are moving or stationary.

According to another aspect of the invention, there is provided an integration of MTNS with microfluidics inside structures that are moving or stationary.

According to a further aspect of the invention, there is provided an integration of MTNS with structures that could form part of any component that is flexible like beams, cantilevers, plates, diaphragms, etc. that are moving or stationary.

According to yet another aspect of the invention, there is provided a method of fabrication of nanoparticle reinforced polymer comprising: performing a partial and controlled reduction of metal salts to nanoparticles by using a curing agent during the preparation process of the polymer.

In some embodiments, performing a partial and controlled reduction of metal salts comprises reducing the metal salts by using the curing agent of the polymer.

In some embodiments, wherein performing a partial and controlled reduction of metal salts to nanoparticles comprises: tuning at least one of optical, electrical, mechanical, thermal and chemical properties of the polymer for various applications by controlling the percentage weight (wt %) of the nanoparticles in the polymer by adjusting an amount of curing agent and a concentration of the metal salts during preparation of polymer.

In some embodiments, the method further comprises using the nanoparticle reinforced polymer for fabricating microdevices and nanodevices having nanostructures with enhanced material properties.

In some embodiments, the tuned optical properties and surface properties of the nanoparticle reinforced polymer aid in immobilizing bio/chemical test material for easier detection by virtue of the uniform distribution of nanoparticles on the surface of nanocomposite.

In some embodiments, the polymer is Polydimethylsiloxane (PDMS).

According to yet a further aspect of the invention there is provided a nanocomposite material fabricated by a partial and controlled reduction of metal salts to nanoparticles by using a curing agent during the preparation process of the polymer.

In some embodiments, the nanocomposite is used for microelectronic and/or electronic sensors and applications.

In some embodiments, the nanocomposite has enhanced mechanical properties that can be used to form part of any component that is flexible like beams, cantilevers, plates, diaphragms, actuators, etc. that are moving or stationary.

In some embodiments, the polymer is Polydimethylsiloxane (PDMS).

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the invention will now be described with reference to the attached drawings in which.

DETAILED DESCRIPTION OF THE EMBODIMENTS OF THE INVENTION

Figure 1:
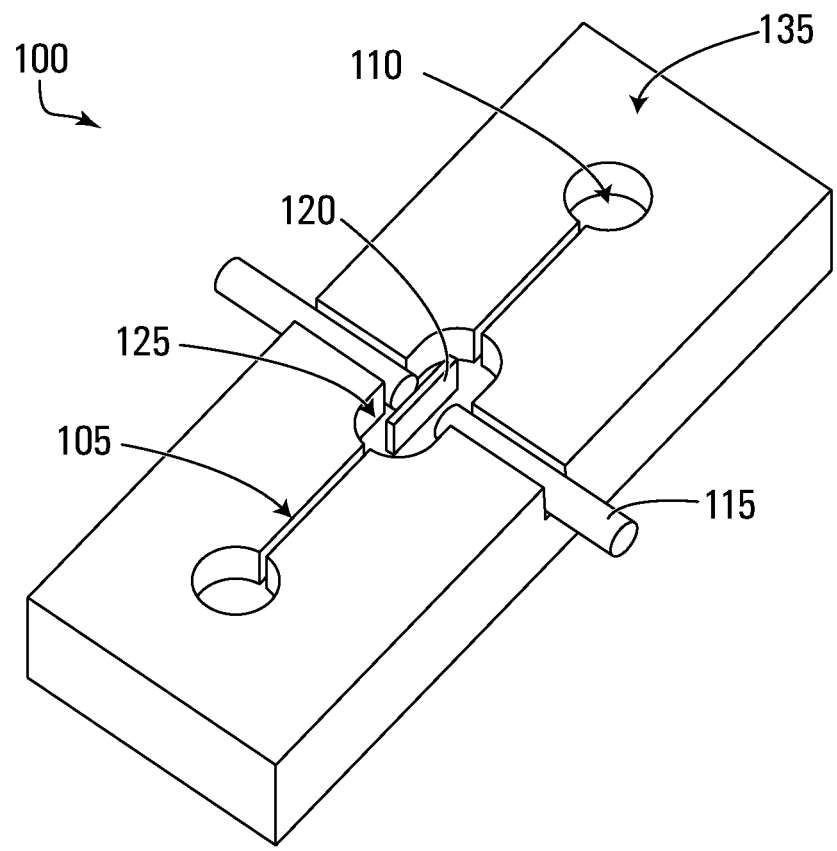
FIG. 1 is a schematic drawing of a proposed microfluidic device according to an embodiment of the invention.

The advantages of microfluidics devices include one or more of, but not limited to, low cost, high throughputs, lower analysis time (faster assays). Applicants have recently developed a microfluidics device by using a glass-Polydimethylsiloxane (PDMS) hybrid platform, in which gold nano-islands are formed on the glass and integrated with a PDMS microfluidic platform. The gold nano-islands on the glass substrates are formed by a novel convective assembly and post-deposition annealing in a (PDMS microfluidics device, however, optical measurements were carried out using a free space optics arrangement. The integration of an optical assembly was not implemented and the measurements were carried out using the free-space optical setup with the help of large spectrophotometer. Due to lack of direct integration of optical assembly with the microfluidic chip, the portability of the device is limited.

Some embodiments of the present invention relate to a microfluidic device integrated with morphologically transformed nano-structures (MTNS). There is a strong desire for the development of a fabrication method that produces nano-structures that are uniform and strongly adhesive to a substrate and that are also compatible with microfluidic applications. Some embodiments of the present invention are suitable for the formation of nano-structures on sensing substrates such as, but not limited to, polymers, glass, silicon or metal. Such materials are compatible with microdevice fabrication. The formation of nano-structures on such sensing substrates according to the inventive process involve tuning the morphology of materials involved by choosing a suitable annealing and/or deposition condition to achieve a suitable surface morphology for use in various chemical or biological sensing applications. Some embodiments of the invention result in a device having a sensing platform including MTNS that detects polypeptides, proteins and other biomolecules that attach themselves to the MTNS. An optical, namely spectroscopic, method may used to detect the molecules and bio-molecules adsorbed on the metallic nanoparticles immobilized in a microchannel of a microfluidic device. Some examples of metallic nanoparticles that may be used in the nano-structures are gold and silver.

Bio-detection can be based on an immunoassay, that is, a specific antigen-antibody interaction which is followed by important changes in the UV-Visible spectrum. Some embodiments of the present invention result in a device that can be used for the detection of bio-molecules such as nucleic acids (DNA, RNA), complex sugars, lipids, etc. and biological entities such as cells and/or viruses that can be adsorbed on metallic nano-structures. Such a device can be used for quantitative analysis of bio-molecules in different environments such as, but not limited to, water, buffers, serum, milk, etc. Some particular applications where such a device may be used include, but are not limited to, clinical analysis and analysis in the field of agriculture.

Innovations in some embodiments of the present invention may include one or more of the following:

1. transforming the morphology of metallic nano-clusters prepared via in-situ synthesis through a reduction reaction to MTNS by post-deposition annealing;
2. using post-deposition annealing to break down nano-clusters and form the MTNS, which are found to be strongly embedded to the substrate surface, which in some embodiments is PDMS based;
3. using post-deposition temperature to have significant effects on adhesion and migration of MTNS into the substrate;
4. optimizing the annealing temperature to yield higher sensitivity as the MTNS have been found to migrate deeper into a PDMS substrate when the annealing temperature is increased, which results in a lower sensitivity to bio-interaction;
5. integrating a MTNS sensing platform into a microfluidic device for the realization of a lab-on-a-chip (LOC) device;
6. integrating of optical fiber into the PDMS microfluidic device, which results in a portable device;
7. sensing of bio-molecular interactions by micro-pumping which enables the handling and usage of small amounts the reagents and bio-species for the bio-sensing in LOCs;
8. integrating of optical, microfluidics and MTNS on a PDMS platform for the realization of low cost optical LOC devices; and
9. monitoring changes in absorption spectra provoked by the bio-interaction when UV-Vis light is coupled onto a sensing platform realized by in-situ synthesis through a reduction reaction to MTNS by post-deposition annealing.

Some embodiments of the present invention involve a method of integration of nano-structures in microfluidic environments, which is highly suitable for the realization of microdevices capable of performing bio-detection. Some embodiments of the present invention may simplify the detection and quantification of bio-molecules by proposing a simple immobilization technique using MTNS on a PDMS substrate by tailoring the nano-structures, which in turn, tunes the optical properties that can be monitored. A proposed method of deposition and tuning the optical properties is further demonstrated for the fabrication of a nano-integrated micro bio-sensor. The micro-fabrication of the proposed device can be carried out in a general laboratory environment. As the device fabrication process is compatible with the batch fabrication and the material cost is low, low-cost LOC devices can be mass-produced.

Some embodiments of the invention may solve a problem related to pre-treatment of biological samples, that is, the separation of undesired biological or chemical substances from matrices such as milk, serum etc., which could reduce the sensitivity of the device. Some embodiments of the invention enable the carrying out of an immunoassay in a miniaturized LOC environment with enhanced sensitivity, thereby reducing reagent volumes, analysis time and cost of an assay.

Some embodiments of the invention provide a simple methodology, i.e. no special chemicals and expensive equipment are necessary, and the deposition and post-annealing are carried out by a simple reduction reaction of an aqueous metallic ion solution with a PDMS substrate. An example of an aqueous metallic ion solution may be a silver nitrate solution. In such an example, very small amounts of silver are necessary for the formation of MTNS and the process is compatible for the fabrication of a low cost LOC device. In-situ synthesis of a sensing platform in a PDMS microfluidic environment may provide the realization of a low-cost LOC device. Some of the benefits described above may aid in minimizing the cost, time and reagent volumes of an assay. Since fabrication materials are less expensive and the fabrication process is, relatively speaking, simple, a micro bio-sensor fabricated according to embodiments of the invention may be single use and/or disposable.

A sensing platform fabricated according to some embodiments of the invention can be integrated into a microfluidic device and utilized for the detection of bio-molecules. The microfluidic device may be fabricated from PDMS, silicon, glass, polymers, metal, ceramic, or some combination thereof.

The present application will describe embodiments of the invention such as, for example, metallic nano particle MTNS formed by in-situ synthesis on a sensing platform in a microfluidic device for the immunoassay for the screening of large biomolecules. A non-limiting example of such a large molecule may include bovine somatotropin. Upon initial testing of the concepts described herein it was found in some situations that the bio-sensitivity of silver nano-clusters formed on a PDMS substrate was somewhat low. This led to a discovery that transforming the morphology of the nano-clusters by post annealing enhanced the sensitivity. According to embodiments of the invention, the annealing temperature can be selected to optimize the sensitivity.

In some embodiments of the invention the sensing platform is integrated into a microfluidics device by using PDMS soft lithography and oxygen plasma bonding techniques. The soft lithography is used for the fabrication of microstructures on the PDMS. In a particular exemplary device the microfluidics device contains a microfluidic cell and sensing wall which are simultaneously fabricated by molding in soft lithography. The oxygen plasma bonding is used to seal the microfluidic cell containing the sensing wall. In some situations the sensing wall cannot be fabricated separately, but must be cast in a single step along with the microfluidic cell.

In some embodiments, a method of bio-sensing using a MTNS integrated microfluidics device fabricated according to embodiments of the invention includes the steps of:
1. integrating a pretreatment apparatus into a microfluidic device;
2. introducing a linker to functionalize a surface of the MTNS in order to bind a desired bio-molecule;
3. introducing an antibody of a desired antigen and recording the absorption spectrum with a UV-Vis instrument;
4. introducing the antigen to be detected and again recording the absorption spectrum with the UV-Vis instrument; and
5. analyzing the change in the absorption spectrum, thereby quantifying the degree of bio molecular interaction between the antibody and the antigen.

In some embodiments of the invention, reagents (the linker, the antibody, the antigen) identified in preceding paragraphs are provided to the bio-sensing platform via capillary inlet tubes. In some embodiments some form of pump capable of pumping small volumes of liquid is used to supply the reagents. After each step, the sensing platform should be rinsed with some type of cleaning solution, such as, for example, a Phosphate Buffered Saline (PBS) buffer solution.

FIG. 1 shows a schematic illustration of an example microfluidic Lab-on-chip (LOC) device 100 with MTNS integrated into the microfluidic device for the detection of biomolecular interaction. In some embodiments, the device 100 as illustrated in FIG. 1 is realized by three fabrication steps, namely, 1) fabrication of the microfluidic platform 135 including the microfluidic channels 105, liquid reservoirs 110, sensing chamber 125 and channel for the optical waveguides 115, 2) bonding of different layers of polymers that collectively form the microfluidic platform 135 and 3) fabrication of the sensing platform represented by the micro sensing wall 120. These steps may not necessarily occur in this particular order and there maybe additional steps as well, as will be described below.

The component of the device that enables detection of the biomolecular interaction is the micro sensing wall 120, which is realized by integrating the MTNS in the microfluidics environment. In order to select a nanomaterial for integration in the microfluidic platform 135 for use in the detection of large biomolecules such as proteins, the nanomaterial should possess qualities such as, but not limited to, 1) strong adhesion to substrates used for the microfluidics fabrication, 2) surface area suitable for binding large biomolecules and 3) narrow optical absorbance properties. In some embodiments of the present invention MTNS nano-structures integrated with a PDMS microstructure form the microsensing wall 120, which can be used in various bioapplications.

FIG. 1 is illustrated to be a microfluidic platform 135 that is a solid substrate having portions that have been microfabricated out. There are two liquid reservoirs 110, one at either end in the longitudinal direction for fluid entry and exit. There is the sensing chamber 125 roughly in the middle of the substrate, which has the appearance of another reservoir. The microfluidic channels 105 in the substrate connect each of the two liquid reservoirs 110 with the sensing chamber 125 to allow liquid to flow from one reservoir to the sensing chamber 125 and then to the other reservoir. Within the sensing chamber 125, the micro sensing wall 120, or more generally, a sensing platform is integrated. It is on this sensing platform that the MTNS nanostructures are formed by using embodiments of the invention as described herein. Also microfabricated into the substrate are channels in which one or more optical waveguides 115 can be included. In some embodiments the optical waveguide 115 may be an optical fiber. In other embodiments the optical waveguide 115 may be an alternative form of waveguide capable of guiding light. The channels used for the optical waveguides allow a light source (not shown) to be supplied to the sensing chamber 125 and directly or indirectly impinge on the micro sensing wall 120 and a light detector (not shown) to monitor and/or measure light from the sensing chamber 125 that may have interacted with the micro sensing wall 120. Also not shown in FIG. 1, there may be a top sealing slab that covers the top of the microfluidic platform.

While FIG. 1 illustrates a particular arrangement for the LOC microfluidic device 100, for example a rectangular substrate having liquid reservoirs at each end of the substrate and the sensing chamber between the liquid reservoirs, one skilled in the art would realize that the layout of the elements is not particularly important. The arrangement of the elements can take many different forms having a basis in that the sensing platform is located in a volume that allows the sensing platform to interact with reagents used in bio-sensing testing and light to interact with the sensing platform and be detected.

An example process for fabricating a device as illustrated in FIG. 1 according to an embodiment of the invention will now be discussed with reference to three steps illustrated in FIGS. 2A, 2B and 2C.

Step 1—Fabrication of Microfluidic Platform

In some embodiments the microfluidic platform is fabricated using Polydimethylsiloxane (PDMS) because of the following properties of this material: (1) PDMS is optically transparent in the visible and a part of the UV region; (2) three dimensional microstructures can be easily fabricated by using soft lithography technologies; and (3) PDMS is bio-compatible.

Alternatively, in some embodiments of the invention the microfluidic platform is fabricated using silicon, glass, polymer other than PDMS or some combination of silicon, glass, PDMS, other polymer, metal, ceramic or combination of them.

Figure 2A:
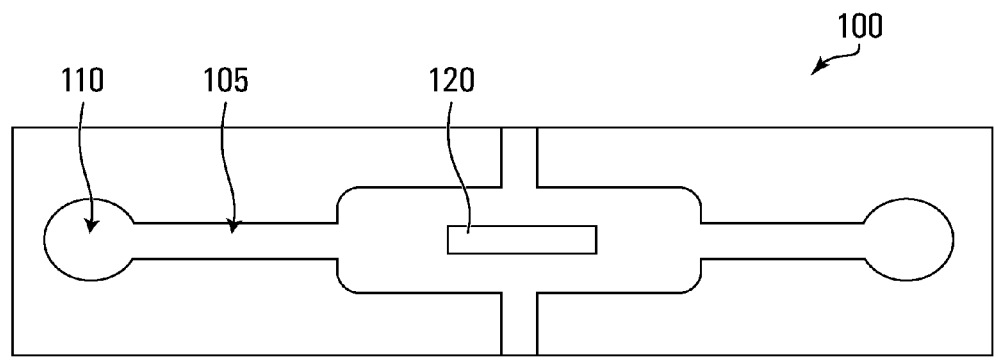
FIGS. 2A, 2B and 2C are a collection of schematic drawings that show a microfluidic platform according to embodiments of the invention at various stages of fabrication.

With reference to FIG. 1 and FIG. 2A, in a particular example of fabricating the microfluidic platform 135, a mold for casting the PDMS in the form of the microfluidic platform is fabricated using SU8 photo-resist. Patterning of SU8 may be done on a silicon wafer using UV photolithography. The PDMS base and curing agent are mixed in a 10:4 weight (wt %) ratio and degassed in a vacuum desiccators to remove the gas bubbles, and then cast in the mold. The SU8 mold can be silanized to promote the easy removal of PDMS structure from the mold.

Step 2—Bonding of Top Surface to Microfluidic Platform

Figure 2B:
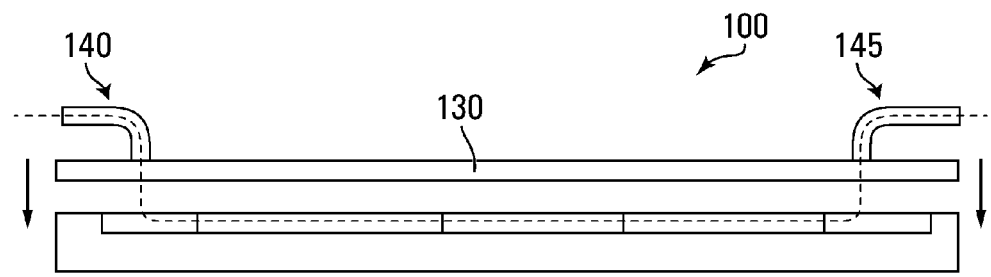
Figure 2C:
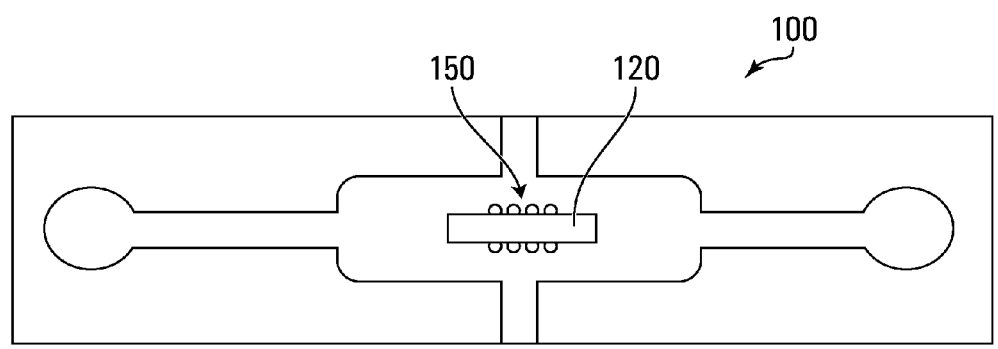

Referring to FIG. 2B, which is a side view of the device 100 shown in FIG. 2A, a thin and flat PMDS slab 130 having a thickness of approximately 2 mm is used to the seal the device 100. Two holes in the PDMS slab 130 align with the liquid reservoirs 110 and allow for inlet and outlet tubes 140,145 to be attached to the slab 130 to supply and extract fluids to the microfluidic platform 135. In some embodiments of the invention the microfluidic platform 135 and the sealing slab 130 are bonded by using oxygen plasma treatment. For example the PDMS microfluidics platform 135 and the flat slab 130 can be exposed to oxygen plasma for approximately 35 seconds and pressed together to bond.

In some embodiments of the invention single mode fibers are used for providing a light source and monitoring the results of the biomolecular interaction occurring in the device. The fiber ends can be cleaved and washed with isopropyl alcohol and inserted into the slots for fibers in the microfluidics platform 135. High precision micropositioners may be used, for example to insert the fibers into the microfluidics platform 135. When bio-sensing is being performed the fibers are connected to a spectrometer and UV-Vis light source, respectively.

This step will be done after the bonding of the top surface to the microfluidic platform.

Step 3—In-Situ Synthesis of Sensing Platform in the Microfluidic Chip

The following is an example of how a silver ion solution is used in synthesizing the micro sensing wall 120 within the microfluidics platform 135. In order to synthesize the micro sensing wall 120 having the MTNS integrated within the microfluidics platform 135, an aqueous silver nitrate ($AgNO_3$) solution is pumped into the PDMS platform described above and maintained therein for a suitable length on time. In this particular example that may be approximately 20 hours. The device is then flushed of the aqueous $AgNO_3$ solution by pumping de-ionized (DI) water through the device for several minutes. Silver nano-clusters are formed on the surface layer of the PDMS microsensing wall by a reduction reaction of $AgNO_3$ reacting with curing agents and oligomers present in the PDMS matrix. In some embodiments the silver nano-clusters will form all over the interior of the device, i.e. within the liquid reservoirs, micro channels, etc. However, the zone where the nano-clusters is most important is the sensing platform (micro sensing wall 120). It is also possible to integrate selectively only on the sensing platform with a more elaborate process. But, from the sensing point of view this is not required. The device is then heated in an oven to transform the silver nano-clusters into the MTNS structures. MTNS 150 synthesized on the micro sensing wall 120 can be seen in FIG. 2C, illustrated as the circles on the micro sensing wall 120.

Figure 18:
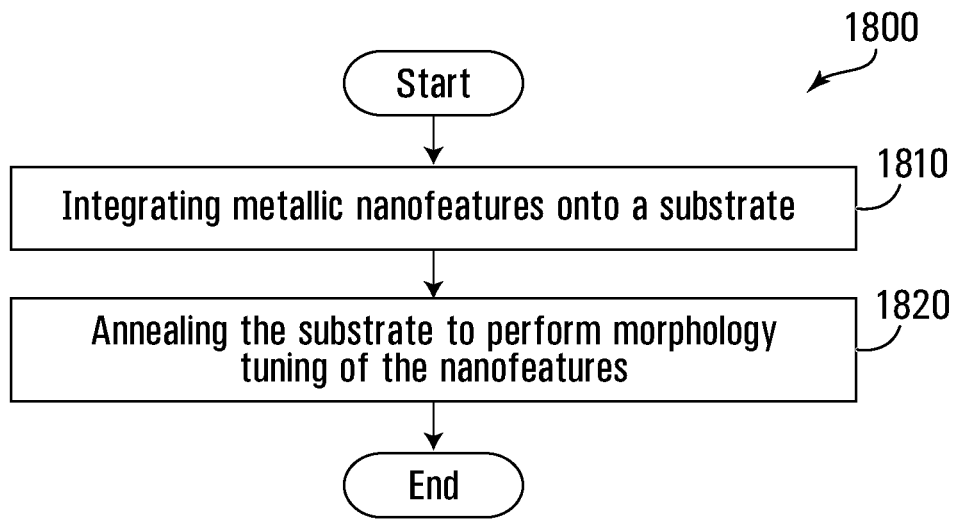
FIG. 18 is a flow chart of a method of fabricating morphologically transformed metallic nano-structures.

FIG. 18 is a flow chart describing a method 1800 according to an aspect of the invention for fabricating a device for bio-sensing. The method includes a first step 1810 of integrating metallic nanofeatures onto a substrate. The method includes a second step 1820 of annealing the substrate to perform morphology tuning of the nanofeatures.

In some embodiments, annealing the substrate involves heating the substrate to a temperature below the melting temperature of the metallic nanofeature material.

In some embodiments, annealing the substrate includes heating the substrate to between 250° C. and 450° C. In some embodiments, annealing the substrate includes heating the substrate to between 300° C. and 400° C. In some embodiments, annealing the substrate includes heating the PDMS substrate to between 340° C. and 370° C. More particularly, the annealing temperature will be determined be the metallic nanofeature material.

Bio-Sensing with MTNS Integrated PDMS

As part of initial testing of the concepts involved with embodiments of the invention, bio-sensing experiments were conducted on a substrate on which MTNS structures were formed. Once a MTNS integrated PDMS micro fluidic platform prototype device was fabricated, experiments were repeated in the device as well.

Preparation of MTNS Integrated PDMS

Figure 3:
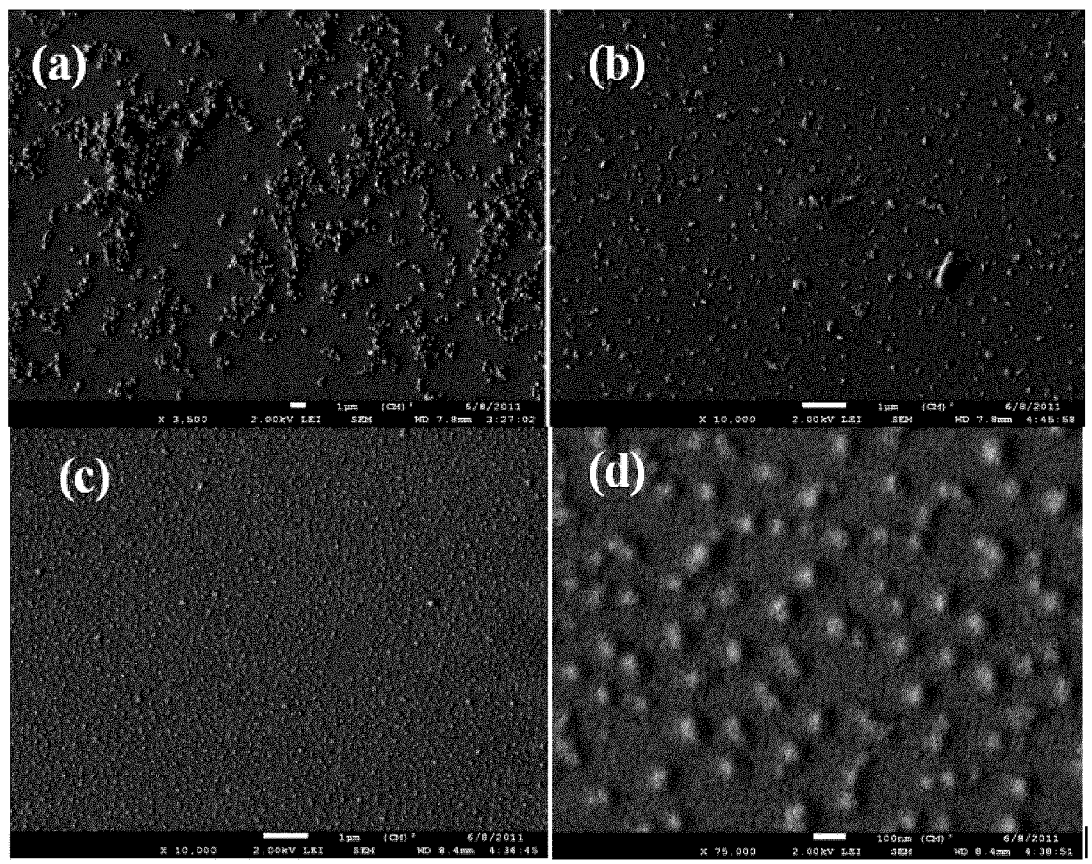
FIG. 3 is a collection of four scanning electron microscope (SEM) images of (a) silver nano-clusters on a substrate, (b) formation of morphologically transformed nanostructures (MTNS) after annealing at 340° C., (c) formation of MTNS by after annealing at 370° C. and MTNS after annealing at 370° C. at higher magnification than (c)

When studying the annealing process related to MTNS formation, samples of 2 mm thick PDMS slabs that had been placed in a solution of aqueous silver nitrate for 20 hours and then annealed at 340° C. and 370° C. were examined. In order to investigate the morphology of the sample, SEM images of the samples were taken. FIGS. 3(*a*), 3(*b*), 3(*c*) and 3(*d*) show the SEM images of the sample taken at various stages of formation of MTNS. The samples had nano-cluster morphology before the annealing as shown in FIG. 3(*a*). With annealing at a temperature of 340° C., the nano-clusters started to disappear and more uniformly embedded MTNS structures were formed on the PDMS surface as can be seen from FIG. 3(*b*). When the annealing temperature was further increased to 370° C., significant removal of nano-clusters from the sample occurred as part of the morphological transformation as can be seen in FIG. 3(c). Atomic Force Microscopy (AFM) characterization of the samples was also carried out to investigate the possible migration of MTNS into the PDMS matrices. While a range of 340° C. to 370° C. was tested for the silver nano-structures, it would be known to one skilled in the art that the temperature range for annealing that results in similar properties of the MTNS will vary depending upon the type of metal used in fabricating the nano-structures.

AFM characterization of the sample also revealed the same morphology as observed in the SEM images. It was discovered that the migration of MTNS into the PDMS matrices, and migration depth depends on the annealing temperature. The average height of the nano-cluster before annealing was around 120 nm above the surface of the PDMS substrate. The height of the MTNS sample with an annealing temperature of 340° C. was around 70 nm above the surface of the PDMS substrate. The height of MTNS sample annealed at the higher temperature of 370° C. was around 20 nm above the surface of the PDMS substrate. Since some silver aggregate particles migrate inside the PDMS, less surface area of the particles are accessible to bind the biomolecules, which may result in less sensitivity for the sample annealed at higher temperatures.

Optical Absorbance Property of the MTNS Samples

Figure 4:
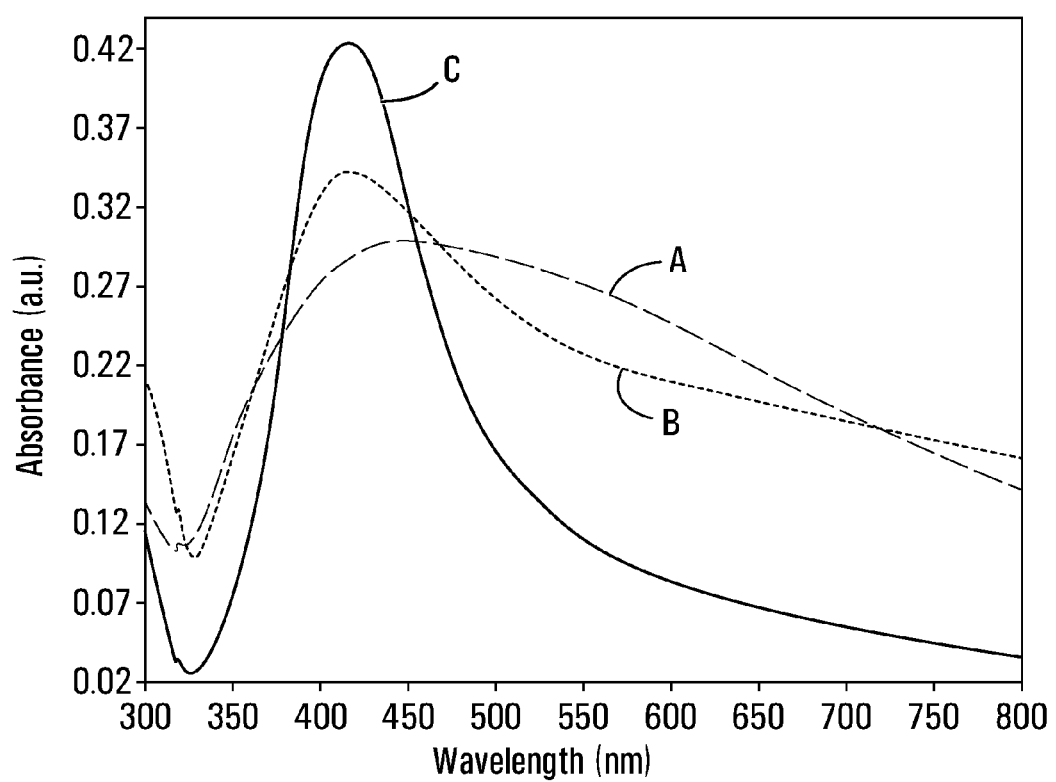
FIG. 4 is a graphical plot of UV-Vis absorbance spectrum of (A) a silver nano-cluster on a substrate, (B) MTNS sample annealed at 340° C., and (C) MTNS sample annealed at 370° C.

As part of the experimental process of developing the invention, the absorbance property of MTNS on PDMS in the UV-Visible range was investigated by using the UV-Visible spectrophotometer. FIG. 4 is a plot of absorbance in which wavelength is plotted on the x-axis in nanometers (nm) and absorbance (a.u.) is plotted on the y-axis. The spectrum of a non-annealed silver aggregate MTNS on PDMS sample is shown in plot A of FIG. 4 having an absorbance maximum at approximately 440 nm and a wide absorption band. The absorption band ranges between 370 to 650 nm. When the sample was annealed at 340° C., the peak of the band "blue shifted" (the peak shifted to a lower wavelength) to approximately 410 nm and the absorption band became narrower, approximately 370 to 510 nm, as shown in plot B of FIG. 4.

The width of the absorption band of the silver aggregates results from near field coupling effects of neighbouring particles in the aggregates, that is, when the distance between the particles is considerably shorter, an electrodynamic interaction mechanism is expected. Upon annealing, aggregates are melting and breaking into smaller particles and also the interparticle distance is increased. As a result, the near field coupling between the particles is decreased, resulting in the blue shift of the absorption band to approximately 410 nm in the example above.

When the annealing temperature was further increased to 370° C., the band became considerably narrower and the absorbance intensity was considerably increased as shown in plot C of FIG. 4.

During the bio-sensing experiments, it was discovered that a higher annealing temperature resulted in a MTNS on PDMS sample having a sharp resonance peak, however, annealing at higher temperatures also resulted in the migration of particles into the PDMS as revealed in the atomic force microscopy (AFM) characterization.

Figure 19:
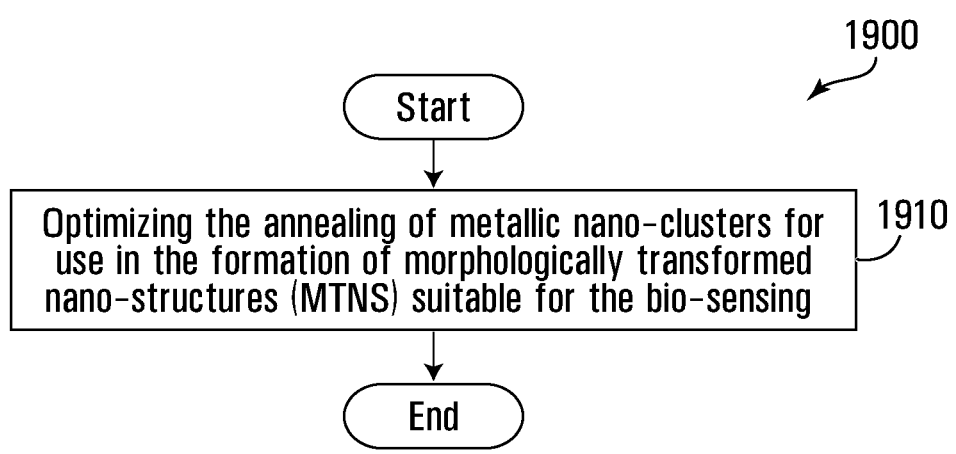
FIG. 19 is a flow chart of a method of optimizing the annealing of metallic nano-clusters.

FIG. 19 is a flow chart describing a method 1900 according to an aspect of the invention. A main step 1910 of the method includes optimizing the annealing of metallic nano-clusters for use in the formation of morphologically transformed nano-structures (MTNS) suitable for the bio-sensing.

In some embodiments, optimizing the annealing of metallic nano-clusters includes selecting a temperature for annealing metallic nano-clusters that is below the melting temperature of the metallic nano-cluster material.

In some embodiments, optimizing annealing the metallic nano-clusters includes selecting a temperature for annealing metallic nano-clusters on a substrate between 250° C. and 450° C. In some embodiments, wherein optimizing annealing the metallic nano-clusters includes selecting a temperature for annealing metallic nano-clusters on a substrate between 300° C. and 400° C. In some embodiments, optimizing annealing the metallic nano-clusters includes selecting a temperature for annealing metallic nano-clusters on a substrate between 340° C. and 370° C.

In some embodiments optimizing the annealing includes selecting a temperature that results in preferred optical properties. For example as noted above, striking a balance between the sharpness of the resonance peak and the migration of the particles into the polymer that results on other characteristics being less favourable.

Bio-Sensing of Recombinant Growth Hormone by using MTNS

In further experimentation, a silver-PDMS substrate was treated with oxygen plasma for 35 seconds to transform the surface of the sample to be hydrophilic.

FIGS. 5A to 5F show various steps in a bio-sensing process using silver-PDMS nanocomposite that has been synthesized according to an embodiment of the invention. In FIGS. 5A to 5F, a single silver nano-particle 500 is illustrated to be embedded in a portion of a PDMS substrate 510 and other particles are shown bonding to the silver nano-particle 500 over the course of the bio-sensing experiment described below.

Figure 5A:
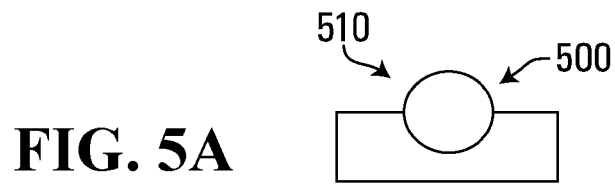
FIGS. 5A to 5F are a collection of schematic diagrams that represent various steps in a bio-sensing process according to embodiments of the invention.
Figure 5B:
Figure 5C:
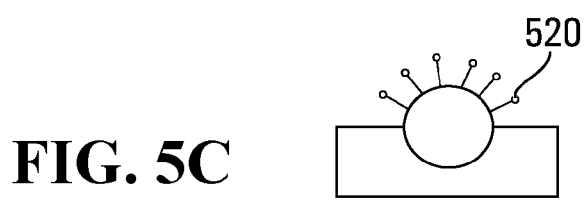
Figure 5D:
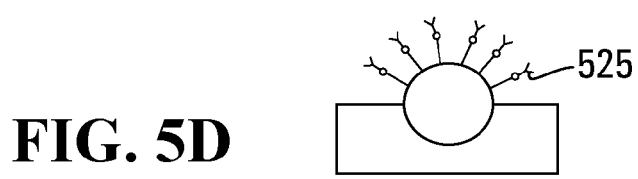
Figure 5E:
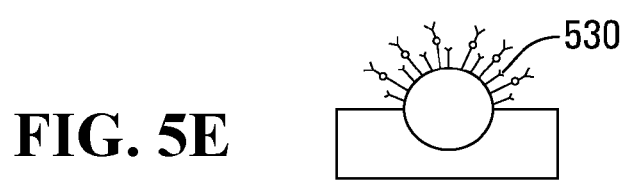
Figure 5F:
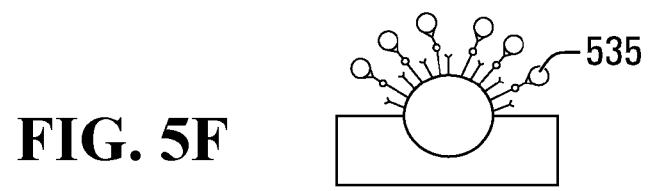

A particular example of implementing the method based on performed experimentation will now be discussed. A PDMS substrate having silver nanoparticles formed on it is shown in FIG. 5A. The PDMS substrate 510 was functionalized, with a small volume (around 150-200 μL) of linker 515, in this particular example mercaptoundecanoic acid (in ethanol). The link is shown in FIG. 5B. Then a cross-linker 520 (N,N'-diisopropylcarbodiimide and N-hydroxysuccinimide) was added the linker 515 and cross-linker 520 are in close proximity to the substrate 510 and silver nanoparticles 500 for approximately one hour in order to covalently attach peptides to the silver nanoparticles. FIG. 5C shows the sample after introducing the linker 515 and cross-linker 520. The sample was then rinsed in a Phosphate Buffered Saline (PBS) solution. The antibody (Anti-rbST 525) corresponding to the rbST 535 was introduced onto the sensing platform and kept in contact with silver nanoparticles for at least one hour. The linker 515 and cross-linker 520 allow the antibody of the rbST to covalently attach to the silver nanoparticles 500. The change of Localized Surface Plasmon Resonance (LSPR) corresponding to the binding of Anti-rbST 525 was measured by a UV-Visible spectrophotometer (LAMBDA 650, Perkin Elmer). The concentration of Anti-rbST 525 on the functionalized PDMS substrate 510 and silver nanoparticles 500 was kept constant and the concentration of antibody was varied between 5 and 10000 ng/mL. The excess antibody is washed away with PBS solution. FIG. 5D shows the sample after the Anti-rbST 525 is adsorbed. A blocker (Blocker 530) (1% non-fat milk powder in a PBS solution) was passed over the PDMS substrate and then rinsed with more PBS. The proteins in the milk powder solution bind to areas not covered by the Anti-rbST 525 and hence act as a blocker. FIG. 5E represents the sample after the Blocker 530 was introduced. Then an rbST 535 solution was introduced to the sample and maintained for one hour. The sample after absorbing the rbST 535 is as illustrated in FIG. 5F. The LSPR spectra were recorded to monitor the change in LSPR corresponding to the antigen-antibody interaction.

Figure 6:
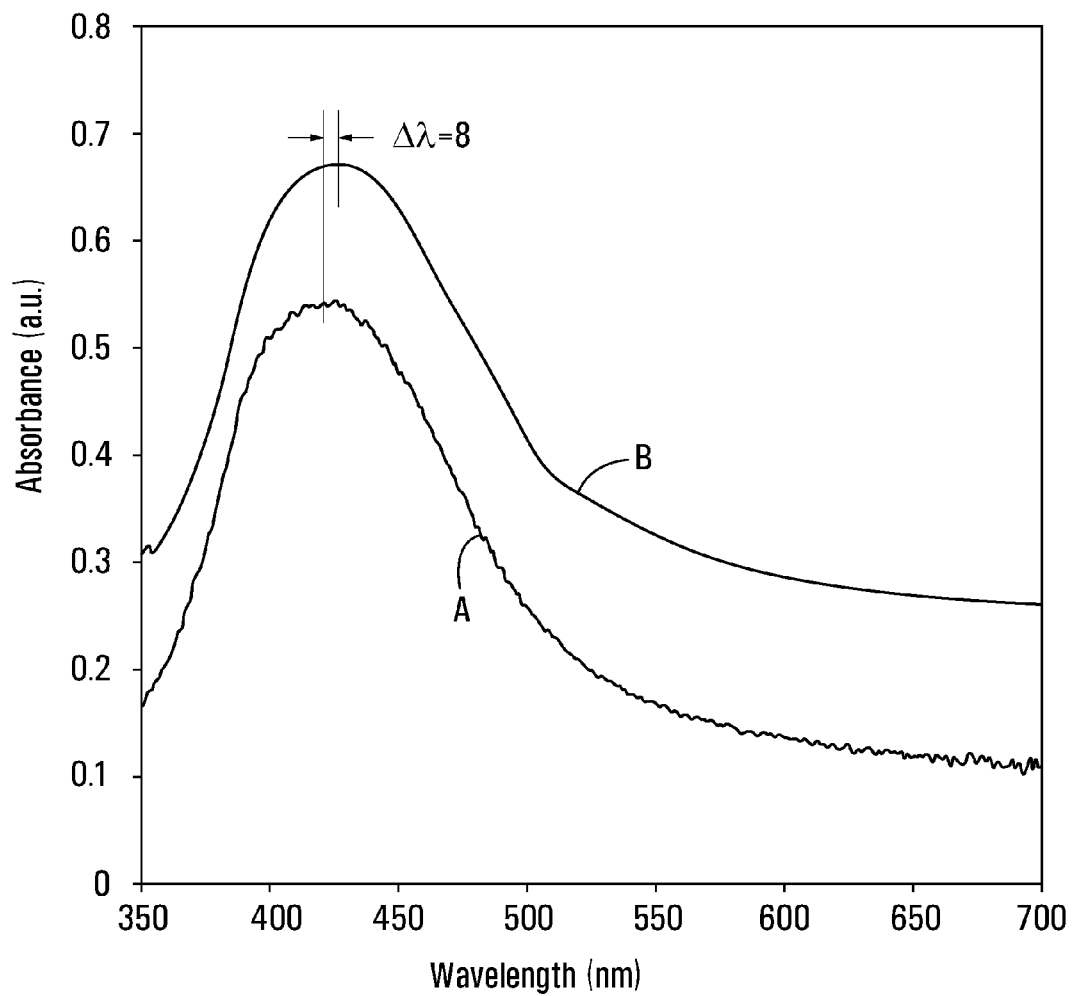
FIG. 6 is a graphical plot illustrating a shift of UV-Vis absorbance spectra of silver-PDMS upon antigen-antibody interaction in which plot (A) shows absorbance spectrum of the silver-PDMS nanocomposite functionalized with an antibody (100 ng/ml) and (B) absorbance spectrum of the silver-PDMS nanocomposite after adding an antigen (150 ng/ml)
Figure 7:
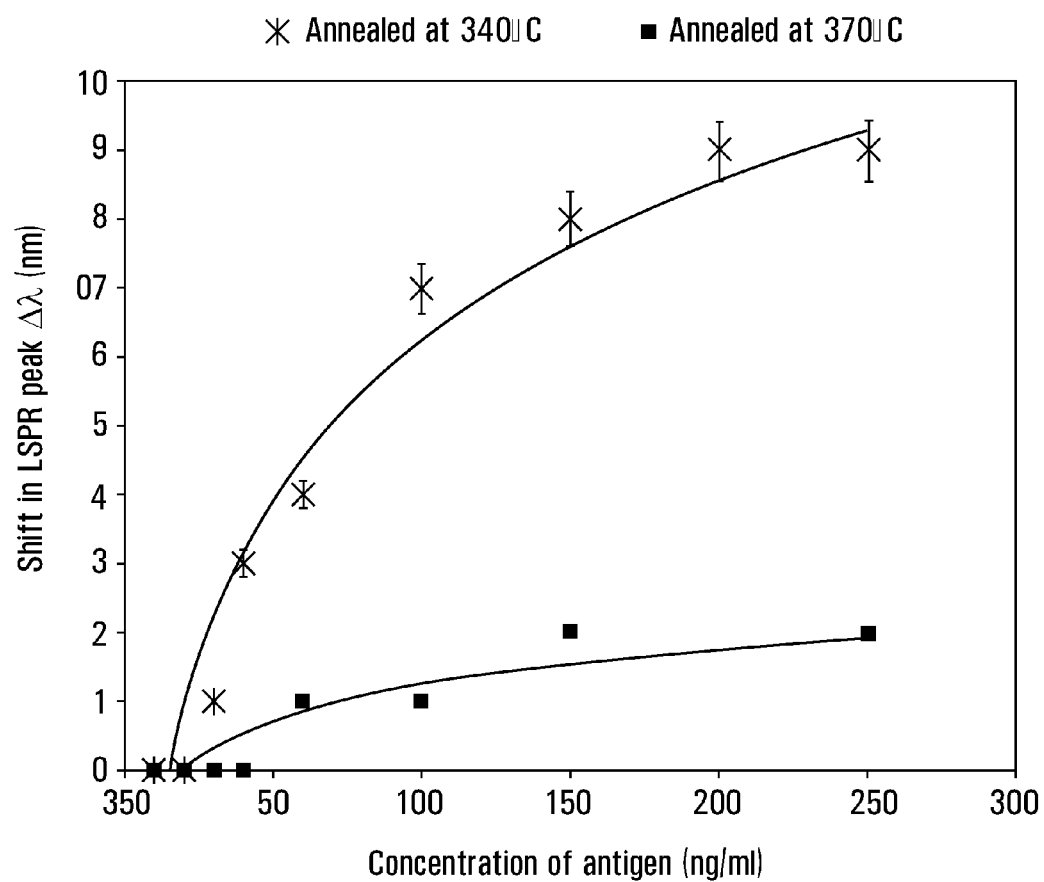
FIG. 7 is a graphical plot illustrating an effect of annealing temperature and concentration of bST (Bovine Somatotropin) on bio-sensing with silver-PDMS substrate.

The samples annealed at 340° C. and 370° C. were tested as part of the bio-sensing experiments. During the bio-sensing process, the spectrum of the PDMS substrate with silver nanoparticle MTNS was recorded during each step of the bio-sensing process. The anti-rbST (100 ng/ml concentration) was added to the surface of the functionalized PDMS substrate with silver nanoparticle MTNS. FIG. 6 illustrates the absorbance of the silver nanoparticle MTNS under different conditions where wavelength in nanometers (nm) is on the x-axis and absorbance (a.u.) is on the y-axis. Plot A of FIG. 6 illustrates the absorbance spectrum of the PDMS substrate with silver nanoparticle MTNS sample after adding the anti-rbST. The antigen (rbST, 100 ng/ml) was added to the sample and kept for one hour, which resulted in a red shift ($\Delta\lambda$) of the absorbance peak of 8 nm as shown in plot B of FIG. 6. In addition, the absorption bandwidth was found to become wider. The experiments were repeated with various concentrations of antigen in order to assess the sensitivity of the platform as shown in FIG. 7. FIG. 7 plots concentration of antigen on the x-axis in nanograms/milliliter (ng/ml) against shift in the absorbance peak or $\Delta\lambda$ in nanometers (nm).

The tested variation of the shift in absorbance band against the concentrations of antigen illustrated in FIG. 7 reveals an almost linear shift in the range of 50 to 100 ng/ml concentration for the PDMS substrate with silver nanoparticle MTNS samples annealed at 340° C. In order to investigate the reproducibility of the results, the bio-sensing experiments were conducted on 5 samples for each concentration. An error bar representing a standard deviation is also included for each plotted point in FIG. 7. The detection limit of the PDMS substrate with silver nanoparticle MTNS samples annealed at 340° C. was found to be as low as 20 ng/ml.

The sensing experiments conducted on the PDMS substrate with silver nanoparticle MTNS sample annealed at 370° C. or above showed less sensitivity, also shown in FIG. 7. Only one or two nanometers of shift was observed for the concentration of 200 to 500 ng/ml of antigen. The reason for the reduction in sensitivity for the samples annealed at higher temperature is likely due to the migration of particles into the substrate as discussed above. As discussed above, AFM revealed that the annealing of the sample at higher temperatures caused the migration of particles deeper into the PDMS, which essentially makes the particles less accessible for the binding of bio-molecules, resulting in reduced sensitivity.

Bio-Sensing in the Lab-On-A-Chip

Figure 8:
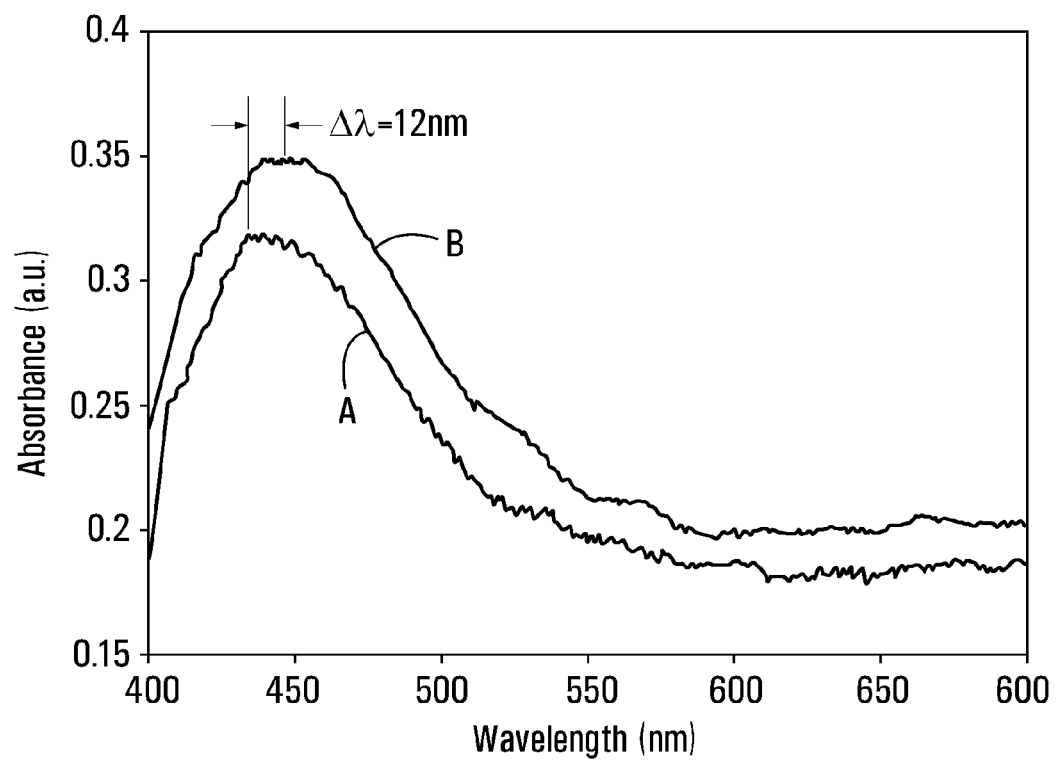
FIG. 8 is a graphical plot illustrating (A) an absorbance spectrum recorded after adding the antibody (100 ng/ml) and (B) spectrum after adding the antigen (100 ng/ml)

The sensing procedure described above with regard to the nanoparticles on a substrate not in a microfluidic device was repeated in a microfluidic device having a silver nanoparticle sensing wall (Lab-on-a-Chip, LOC) according to an embodiment of the invention by pumping the reagents in and out of the device. FIG. 8 illustrates the absorbance of the silver nanoparticle MTNS under different conditions where wavelength in nanometers (nm) is on the x-axis and absorbance (a.u.) is on the y-axis. The absorbance spectrum, shown in FIG. 8, was recorded after 1) providing the antigen and then 2) keeping the antibody in the microfluidic device for approximately one hour. Plot A is the absorbance spectrum with antibody immobilized in the device an d. The spectrum recorded after adding the antigen, identified by plot B in FIG. 8, shows a shift in wavelength of around 12 nm in the spectrum with respect to plot A. The shift of the absorbance peak obtained for the experiments on the substrate closely matched the shift obtained on the LOC device. Several experiments repeated on the LOC device confirmed that an LOC can be realized with the MTNS by preserving the sensitivity obtained on the PDMS substrate with silver nanoparticle MTNS. The shift $\Delta\lambda$ obtained using the LOC device is 12 nm for the concentration of 100 ng/ml as compared to the shift $\Delta\lambda$ of 8 nm obtained using the PDMS substrate with silver nanoparticle MTNS for the same concentration of 100 ng/ml of antigen. This suggests that an LOC my have higher sensitivity in addition to a high throughput.

For the bio-sensing experiments performed using the LOC, very small amounts of reagents and biomaterial were used. For each step in the bio-sensing, less than 0.1 ml of solution was sufficient to carry out the sensing experiments in the LOC. However, in comparison, the experiments involving the PDMS substrate with silver nanoparticle MTNS required around 1.0 ml of reagents for each of the steps.

Figure 20:
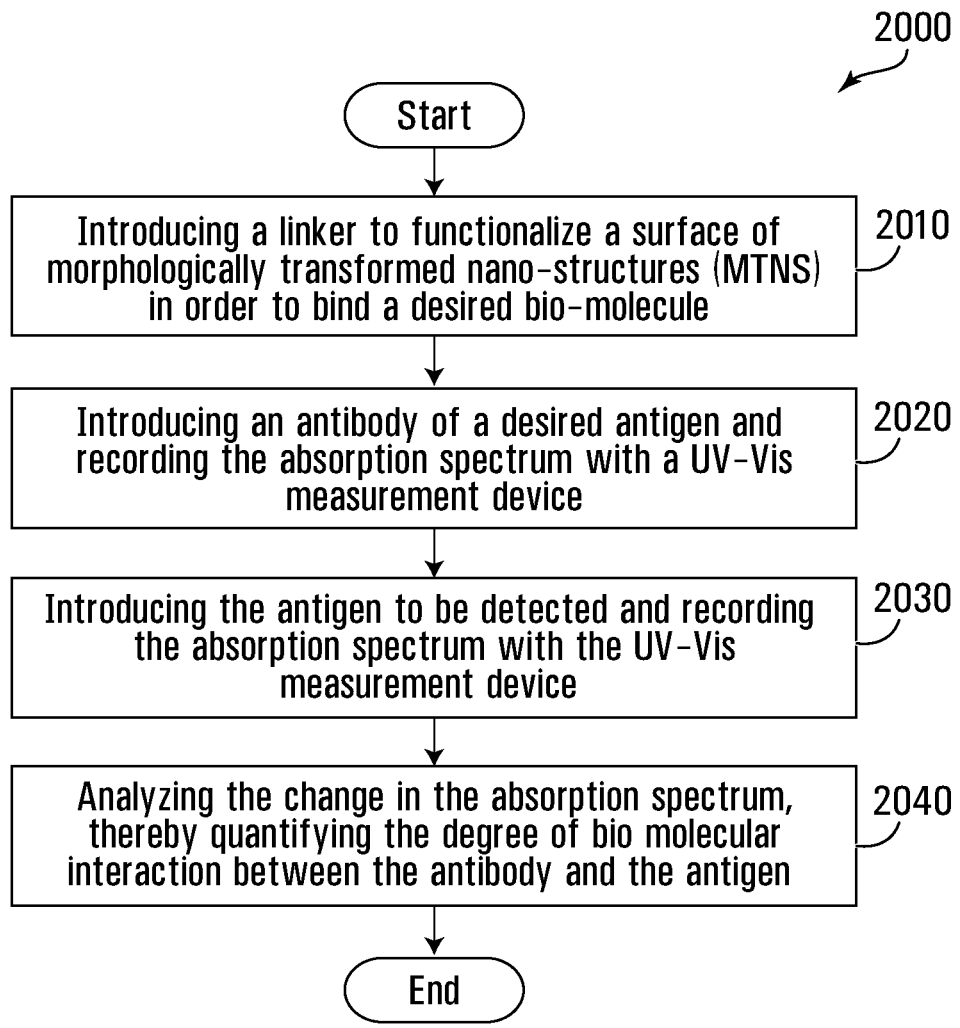
FIG. 20 is a flow chart of a method for performing bio-sensing using a device having morphologically transformed metallic nano-structures according to embodiments of the invention.

FIG. 20 is a flow chart describing a method 2000 according to an aspect of the invention for performing bio-sensing. The method includes a first step 2010 of introducing a linker to functionalize a surface of morphologically transformed nano-structures (MTNS) in order to bind a desired biomolecule. A second step 2020 includes introducing an antibody of a desired antigen and recording the absorption spectrum with a ultraviolet-Visible (UV-Vis) measurement device. A third step 2030 includes introducing the antigen to be detected and recording the absorption spectrum with the UV-Vis measurement device. A fourth step 2040 includes analyzing the change in the absorption spectrum, thereby quantifying the degree of bio molecular interaction between the antibody and the antigen.

Various applications and devices that can be fabricated by using the proposed in-situ synthesis of MTNS are described below with reference to FIGS. 9 to 13.

Figure 9A:
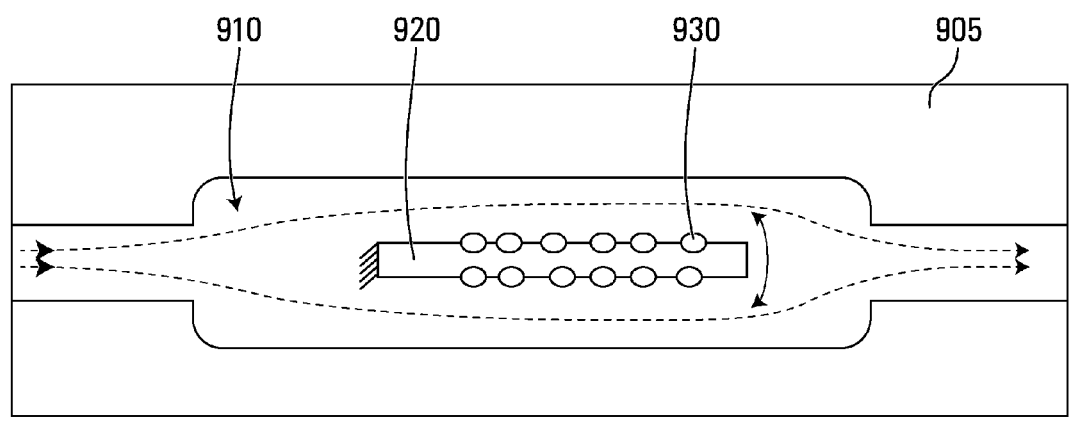
FIGS. 9A and 9B are schematic diagrams of top and side views of an MTNS integrated micro cantilever according to an embodiment of the invention in a microfluidics channel.
Figure 9B:
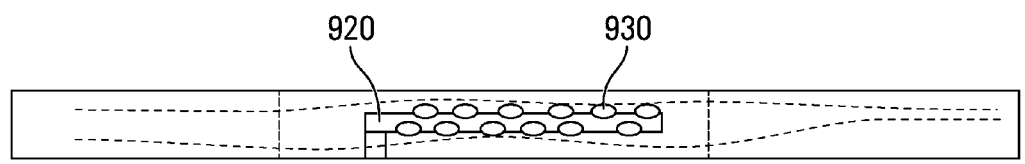

FIGS. 9A and 9B illustrate a top view and a side view, respectively, of synthesis of MTNS integrated in a microfluidic channel of a micro cantilever for the enhanced sensing of biomolecules, flow sensing, etc. The microfluidic channel 910 is within a polymer 905. The micro cantilever 920 is located within the microfluidic channel 910. The MTNS are represented as the circles 930 on the micro cantilever 920. The dotted lines in FIGS. 9A and 9B represent the flow of a sample being analyzed within the device.

Figure 10:
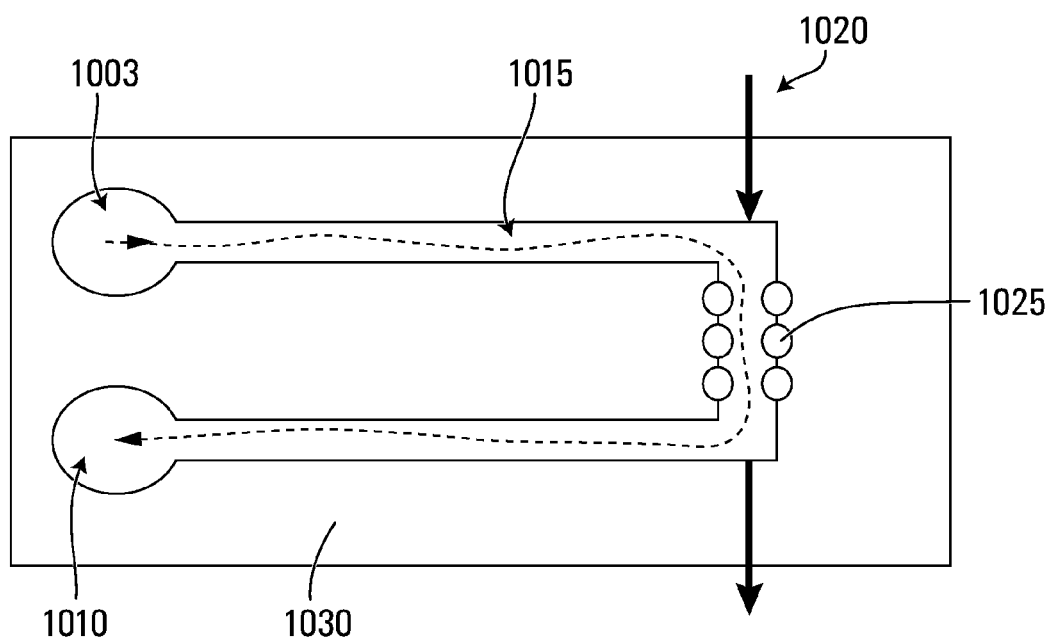
FIG. 10 is a schematic diagram of a MTNS in U-shaped microchannel of the liquid core waveguide for the evanescence based bio-sensing.

FIG. 10 illustrates synthesis of a U-shaped microfluidic channel with a liquid core waveguide and MTNS integrated evanescence based biosensor. Reservoirs 1005 and 1010 and microfluidic channel 1015 are shown within a polymer substrate 1030. The MTNS are represented as the circles 1025 on the edges of the bottom of the "u" of the microfluidic channel 1015. The dotted lines in FIG. 10 represent the flow of a sample being analyzed within the device. This figure illustrate that part of the microfluidic channel 1015 can also be used as an optical waveguide 1020 that light can be injected into and after the light has interacted with the MTNS structures be detected. While this figure shows a U-shaped channel, it is to be understood that alternative shapes of the microfluidic channel integrated with MTNS and microfluidics channel can be used.

Figure 11A:
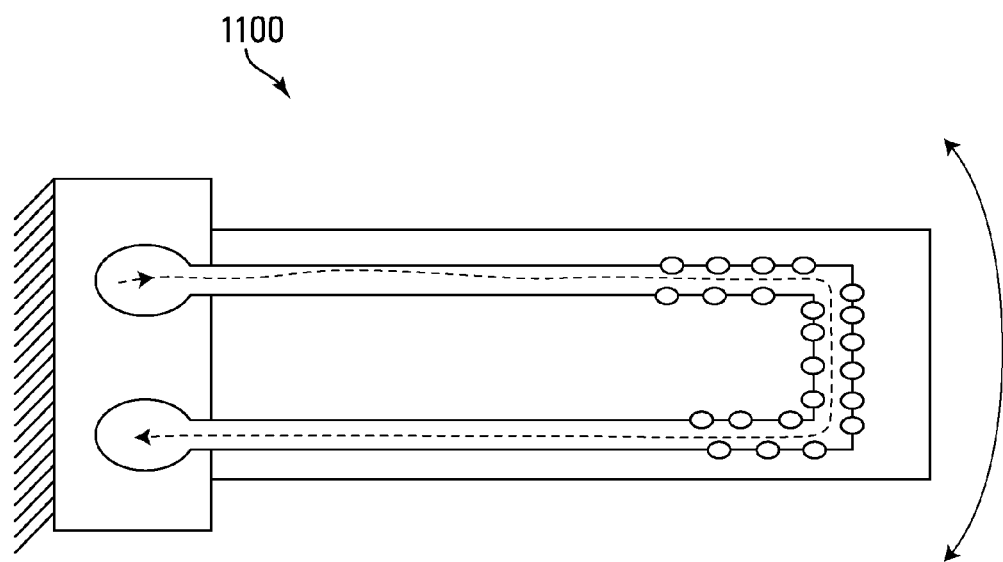
FIGS. 11A and 11B are schematic diagrams of top and side views of a MTNS integrated liquid core waveguide in a micro-cantilever for enhanced micro-bio-sensing.
Figure 11B:
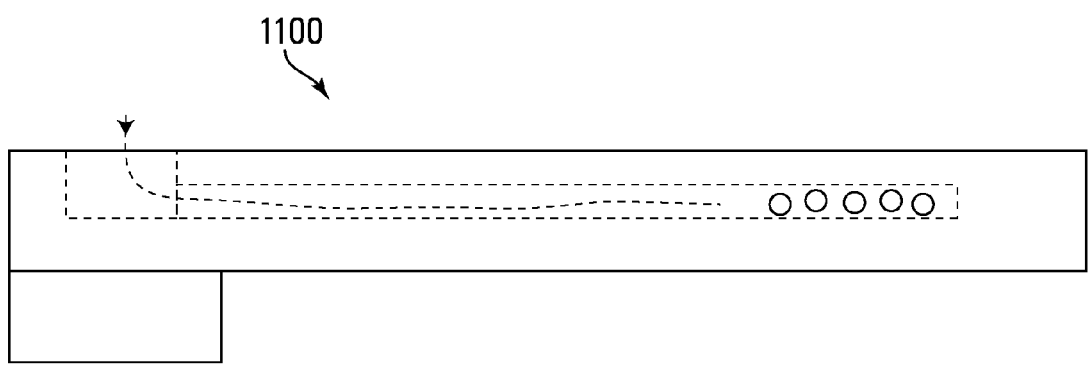

Synthesis of MTNS in the microchannel in a micro cantilever for enhanced bio-sensing is illustrated in FIG. 11. MTNS are integrated all along the microchannel. This figure represents any shape of MTNS integrated microfluidics that is buried inside any moving micromechanical structure such as microcantilever. The microcantilever 1100 in FIG. 11 is essentially of the same type as that microfluidic device in FIG. 10, but is being used as a cantilever device. While this figure shows a U-shaped channel, it is to be understood that alternative shapes of the microfluidic channel integrated with MTNS and microfluidics channel can be used. In this case, microfluidic channels are first fabricated inside the microcantilever and MTNS are integrated inside the microfluidic channels. As in FIG. 10, at least a portion of the microfluidic channel may be used as optical waveguide.

Figure 12:
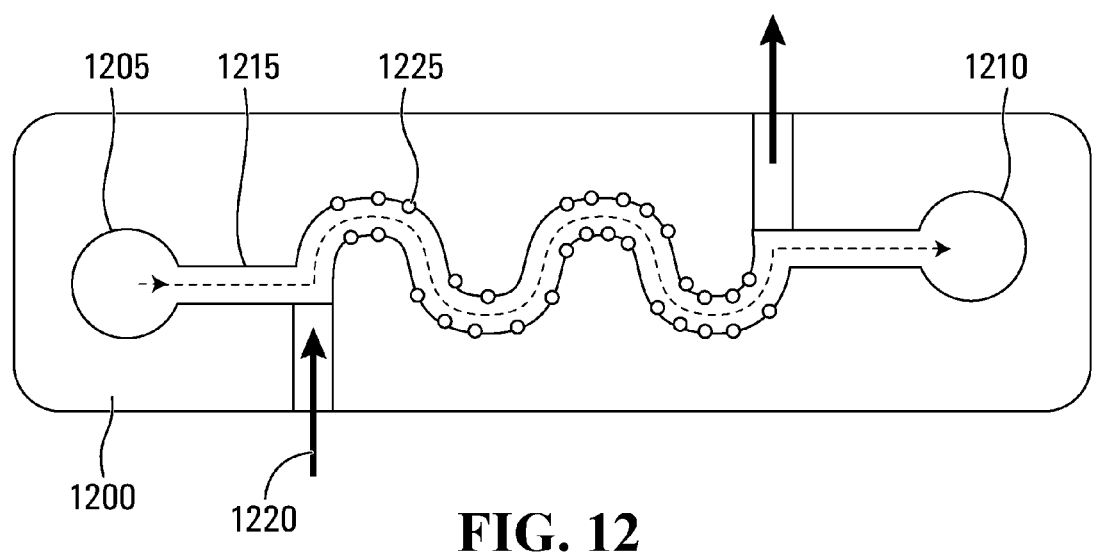
FIG. 12 is a schematic diagram of cascaded U-bends for enhanced evanescence sensing.

In-situ synthesis of MTNS integrated, cascaded U-bends for the enhanced evanescence sensing is illustrated in the example of FIG. 12. MTNS are integrated all along the microfluidic channel. Reservoirs 1205 and 1210 and microfluidic channel 1215 are shown within a polymer substrate 1200. The MTNS are represented as the circles 1225 on microfluidic channel 1215. The dotted lines in FIG. 12 represent the flow of a sample being analyzed within the device. The arrows entering 1220 and exiting the microfluidic channel 1215 represent the beginning and end of the optical waveguide path. This figure illustrates a particular shape of microfluidic channel integrated with MTNS and that a portion of the microfluidic channel itself is used as optical waveguide allowing evanescent coupling to be used for detection. While this figure represents a particular shape of the microfluidic channel, it is to be understood that any alternative shape may also be used.

Figure 13A:
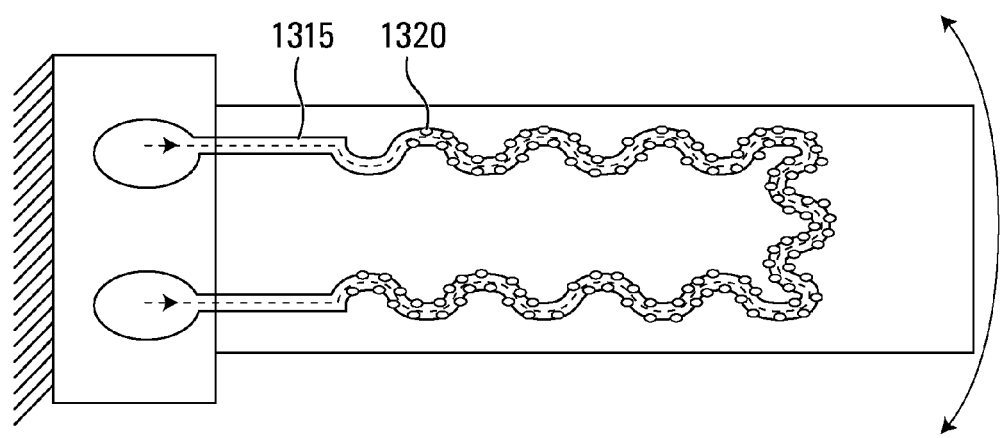
FIGS. 13A and 13B are schematic diagrams of top and side views of a MTNS integrated cascaded U-bend in a microcantilever.
Figure 13B:
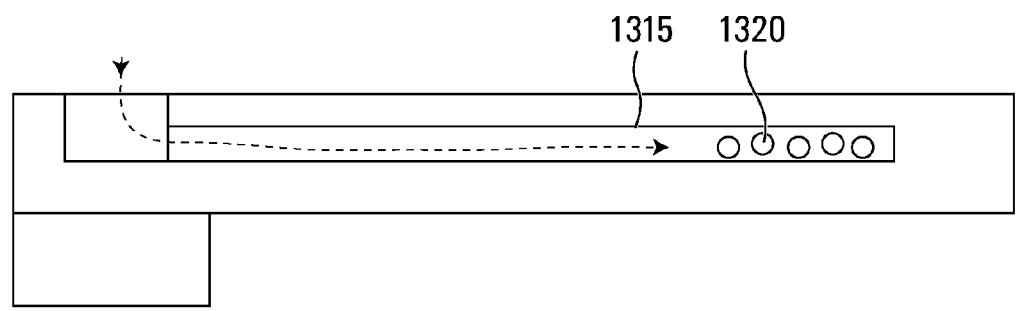

FIGS. 13A and 13B illustrate an example similar to FIG. 11, but the microfluidic channel, while having an overall U-shape, is somewhat serpentine in nature. In FIG. 13 MTNS are integrated all along the microchannel as represented by the circles within the microfluidic channel 1315.

Some embodiments of the invention involve the integration of MTNS with structures that are moving or stationary.

Some embodiments of the invention involve the integration of MTNS with microfluidics inside structures that are moving or stationary.

Some embodiments of the invention involve the integration of MTNS with structures that could form part of any component that is flexible like beams, cantilevers, plates, diaphragms, etc. that are moving or stationary.

FDTD Modeling

The following sections are a discussion of performing a finite difference time domain (FDTD) modeling of Morphologically Transformed Nano-structures (MTNS) performed while investigating the invention.

FDTD modeling solves the Maxwell's differential equations by discretizing using central difference in space and time followed by solving them numerically by computers. Commercially available softwave called Rosft FullWAVE, for example, can be used for the FDTD simulation of MTNS structure. The MTNS structure is realized by widely separated nano-structures; hence for simplifying the modeling of MTNS, the nanostructure of the MTNS structure is approximated to a nanohemisphere. In order to demonstrate the bio-sensing abilities of MTNS structures, gold nano-islands were used as gold and silver have a similar fabrication and bio-sensing procedure for the MTNS structure.

Modeling of Gold Nanohemisphere

As the simulation domain is discretized into small elements called grids or mesh, the size of the mesh decides the accuracy of the model. Hence, in the beginning of the modeling, the dependence of the sized of the mesh on the results is investigated.

Figure 14A:
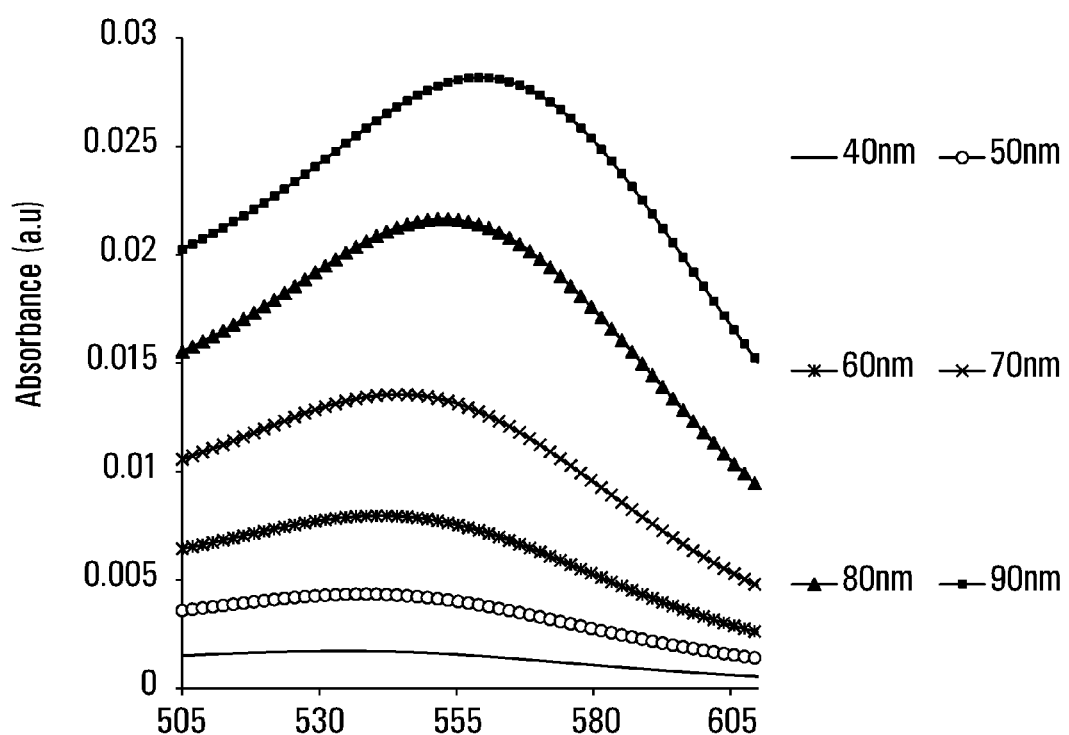
FIG. 14A is a graphical plot of an optical absorbance spectrum of a gold nanohemisphere.

The simulation of the nanostructure with various mesh elements determined that the peak wavelength of the optical absorbance spectrum was within 535 to 565 nm for gold nanohemispheres ranging in size from 40 nm to 90 nm as shown in FIG. 14A. FIG. 14A illustrates the simulated absorbance of the gold nanohemispheres where wavelength in nanometers (nm) is on the x-axis and absorbance (a.u.) is on the y-axis. When the size of the mesh was reduced to 1 or 2 nanometers, the difference in the peak absorbance wavelength was within 2 nm. Therefore the subsequent modeling was carried out by using the mesh elements of 1 nm.

Dependence of the Size of the Nanohemisphere on the Optical Absorbance Spectrum

Figure 14B:
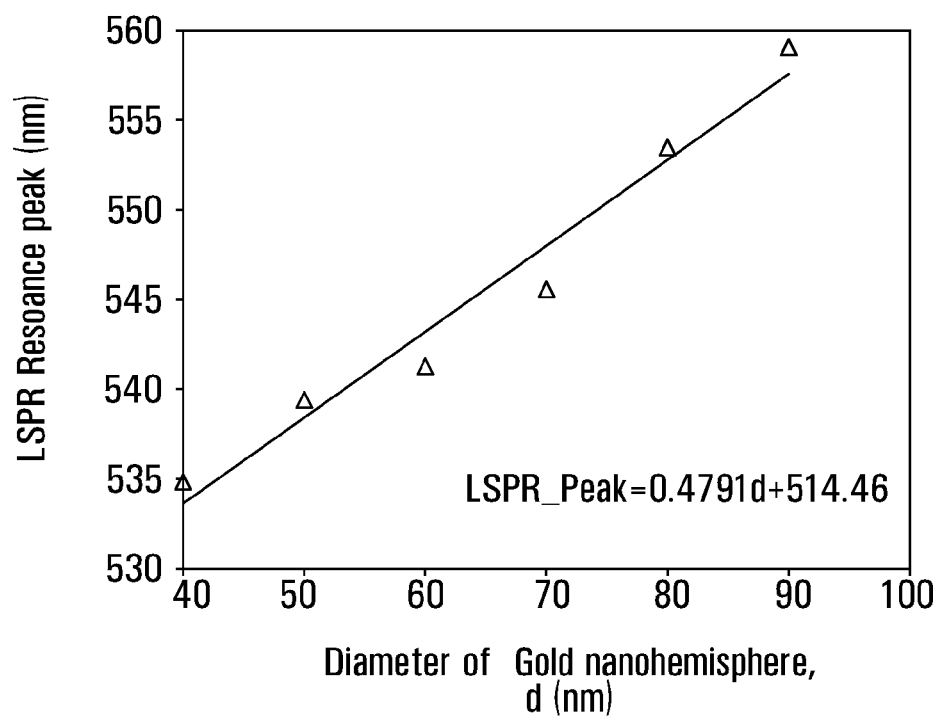
FIG. 14B is a graphical plot of a red-shift of peak wavelength against the size of a gold nanohemisphere.

The simulation carried out by increasing the diameter of the gold nanohemisphere shows that the optical absorbance peak is gradually shifted towards higher wavelengths as shown in FIG. 14B. FIG. 14B illustrates the simulated resonance peak of the different size gold nanohemispheres where the diameter of the gold nanospheres in nanometers (nm) is on the x-axis and resonance peak wavelength, also in nm, is on the y-axis. The spectrum shows an increment in absorbance peak and also the intensity of absorbance against the diameter of the gold nanohemisphere. The diameter of the gold nanohemisphere was simulated from 40 nm to 90 nm. A linear trend in the absorbance peak was observed as shown in the FIG. 14B. An increment of each 10 nm of the diameter of the nanohemisphere showed an increment of the absorbance peak wavelength of approximately 5 nm.

Sensitivity of the MTNS Sample on the Absorbing Protein Layer

It was important to investigate the sensitivity of the optical absorbance peak in relation to the refractive index, as during the bio-sensing process, analytes bind to the gold nanostructure and the refractive index of the environment of the gold nanostructure changes, which results in a shift of the band. For that, a model composed of gold nanohemispheres with a dielectric layer (equivalent of protein layer) covering the whole surface area of the nano-structures was used.

The thickness and the refractive index of the absorbing protein layer could affect the optical absorption property of the nanostructure, hence, the effects of both the thickness and the refractive index were theoretically investigated. In the simulation, the refractive index was kept constant and the thickness of the protein layer was varied from 0 to 140 nm. Then the simulation was repeated for various thicknesses and various refractive indices.

The refractive index was varied from 1.3 to 1.5 as most biomolecules have a refractive index in this range. The results of simulations carried out to investigate the effects of thickness of the protein layer and the refractive index shows (FIG. 15) that the absorbance peak wavelength is very sensitive only to a thin layer of protein of 60-70 nm, absorbing to the MTNS structure. The simulated sensor was saturating above the thickness of 70-80 nm. Hence, the MTNS structure is highly suitable for the sensing of surface-assisted phenomena, which is highly desirable for the specific detection of antigen-antibody interaction occurring on a sensing substrate.

Figure 15:
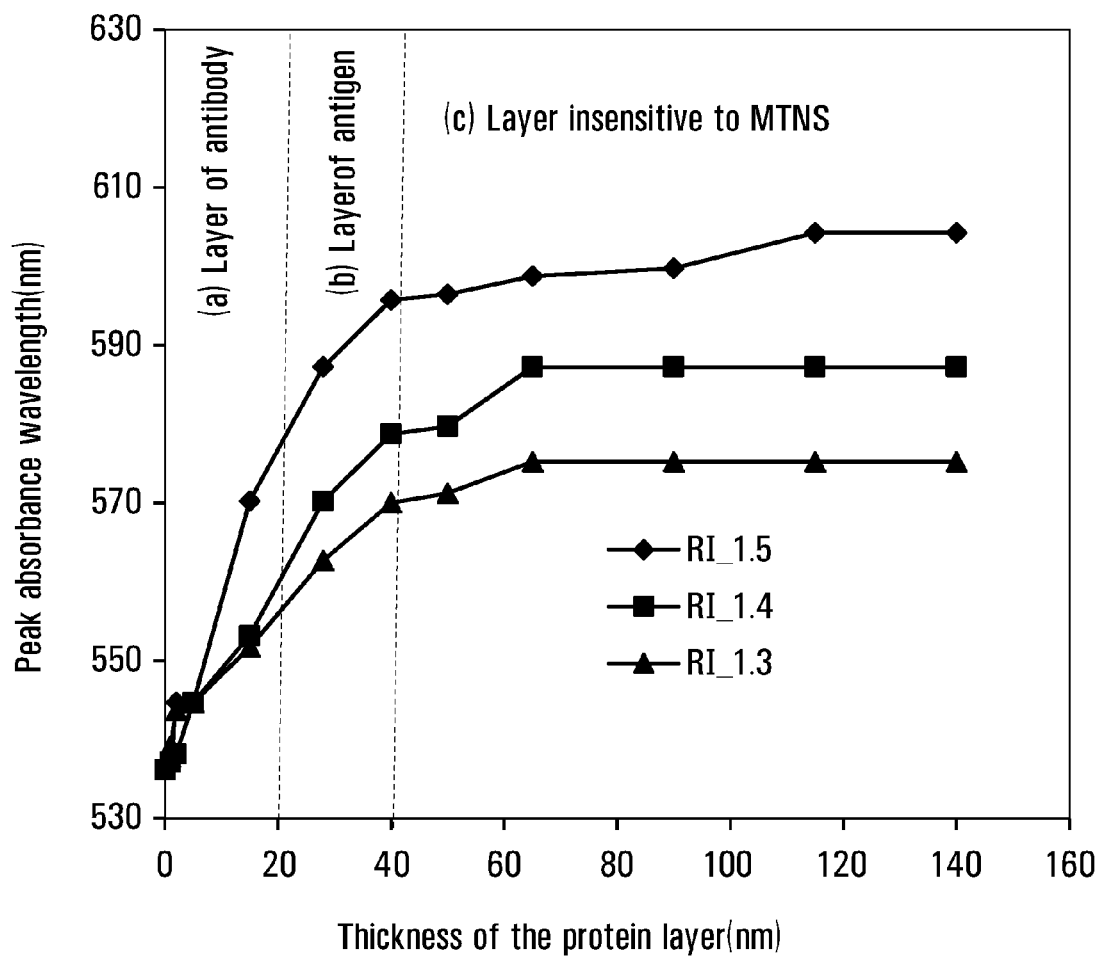
FIG. 15 is a graphical plot of variation of peak absorbance wavelength against thickness of a protein layer coating a MTNS structure.

FIG. 15 illustrates the simulated absorbance wavelength in nanometers (nm) on the x-axis and peak absorbance wavelength, also in nm, is on the y-axis. In FIG. 15, three regions of the thickness of the protein layer could be identified. Since the size of a large biomolecule is within 10 to 20 nm, the antibody of the protein layer adsorbing to the MTNS structure for the sandwiched immunoassay is highly sensitive. Subsequently, the antigen was added to the antibody layer and formed a thick layer of 40 to 50 nm of biomolecules through the biochemical reaction. The region above 60-70 nm is insensitive; hence the MTNS structure was determined to be a highly suitable sensing platform for the detection of biomolecules including the large biomolecules such as protein and polypeptides.

Modeling of Morphology Transformation

Figure 16:
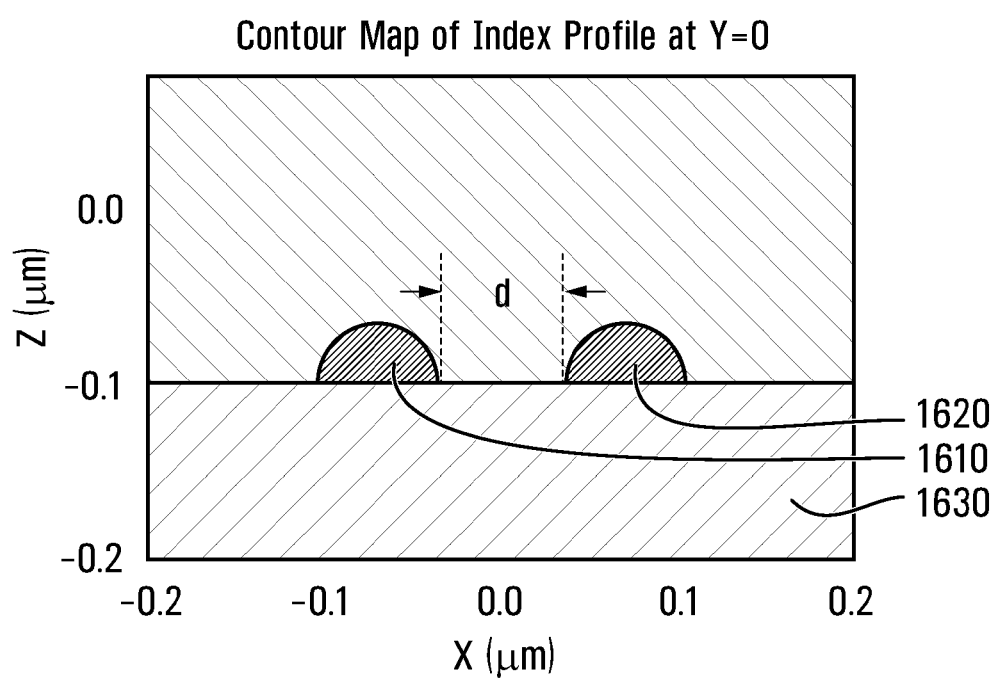
FIG. 16 is a graphical plot of a FDTD model of MTNS morphology.

During the morphology transformation, by using a heat treatment, the gold aggregates melt and form widely separated nano-structures. Herein the melting temperature of nanostructures is highly depressed from their bulk from. Hence, the heat treatment of aggregated nanostructures by using lower temperature is sufficient to achieve a morphological transformation. The FDTD model used for the investigation morphological transformation is shown in FIG. 16. FIG. 16 illustrates a contour map profile used in the simulation of two metallic nanospheres 1610 and 1620 on a substrate 1630. The inside edges of the two metallic nanospheres 1610 and 1620 are shown to be separated by a distance d. The effect of the separation distance d of two nano-structures on the optical absorbance property of the MTNS is studied in this model.

Figure 17:
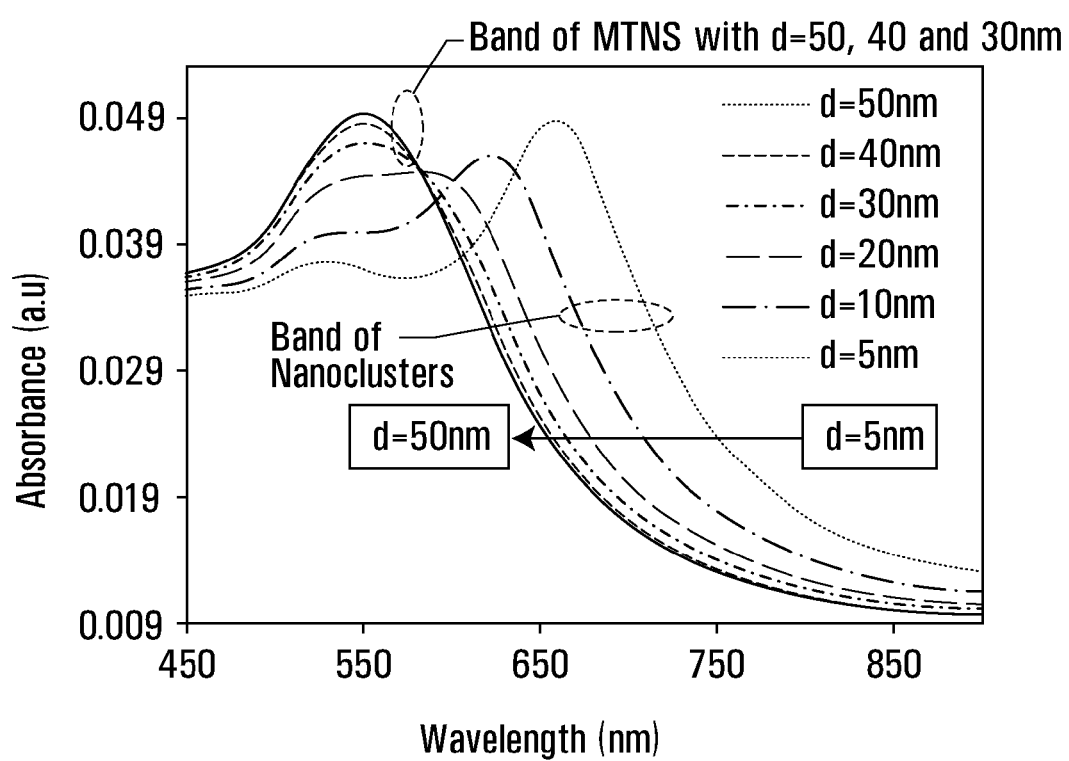
FIG. 17 is a graphical plot of optical absorbance spectrum of MTNS structures against a particle separation distance, d.

FIG. 17 illustrates the simulated absorbance for various spacings of the gold nanospheres where the wavelength in nanometers (nm) is on the x-axis and absorbance wavelength, (a.u.) is on the y-axis. FIG. 17 shows the simulation results of the interparticle coupling effects on the absorbance property of the MTNS structures. Two nanohemispheres having a diameter of 70 nm were used in the simulation. The separation distance, d of the two nano-structures was increased from 5 nm to 50 nm and the absorbance property of the MTNS was computed. When the particle separation distance was 5 nm, the optical absorbance spectrum was wide and also showed two resonance peaks, one small peak at 525 nm and a high peak at 660 nm as shown in FIG. 17. When the d was increased, it was found that the intensity of the peak was decreased and also the smaller peak moved towards the higher wavelength and the higher peak moved towards the lower wavelength. The d was further increased to 20 nm, which resulted in a single and wide absorbance peak. When the d was 30 nm or above a single and narrow absorbance peak was observed at 545 nm.

The simulation results show that the optical absorbance band of closely packed particles have a wide band. The refractive index sensitivity of such a closely packed nanocluster and MTNS structure was experimentally investigated to determine the particular variables that could be varied in order to cause the MTNS structures to exhibit an improved sensing platform. The effect of the separation distance of two nano-structures in the MTNS was studied, and it was discovered that by properly transforming the morphology, the desired optical absorbance band could be obtained for different bio applications.

The effects of absorbing the bio-molecule layer of various thicknesses and the refractive indices on the MTNS structure were also investigated. It was discovered that the optical absorbance property of the MTNS remains unchanged when the thickness of the bio-molecule layer was above 70 nm, which makes the MTNS useful for a highly specific detection of biomolecules adsorbing to it, as only the events taking place in the close proximity of MTNS are detected, and suitable for large molecules such as protein or polypeptides.

Conventional methods for the formation of nano-island structures or the deposition of nanoparticles on a sensing substrate are by thermal evaporation, sputtering or convective assembly or layer-by-layer deposition, which all typically involve using expensive apparatus. Using various expensive deposition methods, a thin layer of gold film is deposited and annealed to form nano-island structures, which suffer from several disadvantages, such as poor adhesion and incompatibility to the integration in the microfluidic devices. Therefore, a novel and simple method of forming MTNS structure on the sensing substrate is presented in this invention.

According to some embodiments of the invention there is provided a MTNS structure that is highly suitable for the realization of a lab-on-a-chip device, due to its compatibility with microfabrication combined with the enhanced sensitivity to the specific detection of large biomolecules, as verified by the FDTD modeling.

According to some embodiments of the invention there is provided an enhanced optical detection system for determining the position of the gold band and its change in response to the antigen-antibody interaction by a simple transmission mode spectroscopy.

According to some embodiments of the invention there is provided a formation technique of MTNS that is compatible for any metallic nanoparticles on any row material of the fabrication of microdevices such as glass, PDMS or any transparent substrate; hence the invention is the compatible for the fabrication of low-cost lab-on-a-chip devices.

According to some embodiments of the invention there is provided immobilization of metallic nanoparticles directly on micromachined or soft lithographically patterned microfluidic structures, thereby simplifying the fabrication process for the realization of a lab-on-a-chip.

According to some embodiments of the invention there is provided a fabrication of the gold multi-layers by angled convective assembly on a functionalized glass substrate and morphology tuning to yield MTNS samples.

According to some embodiments of the invention integration of MTNS by the proposed process is also useful for the fabrication low-cost micro devices for various optical, electrical or mechanical sensors and actuators.

According to some embodiments of the invention there is provided integration of MTNS in a device where one or many types of transduction technique is used, such as, electrical, optical, chemical and micromechanical.

Tuneable Nano-Integrated Functional Nanocomposite Polymers Synthesized via In-Situ Reduction and Mechanical Stimulation As indicated above, the demand for nanoparticle reinforced polymers is huge because of its numerous application potentials. Various approaches are known for the synthesis of nanocomposite. A common method is mixing nanoparticles in a powdered form with a given polymer. The nanoparticles may be for example conductive fillers to vary the conductivity of the polymer. The amount of nanoparticle may be varied based on an application for which the nanoparticle reinforced polymer may be used.

In some embodiments, in order to obtain a conductive polymer nanocomposite, the polymer and metal nanoparticles are mixed and when the percentage by weight of the nanoparticles is at or above 50-60%, that is when the percolation threshold is crossed, the conductivity of the nanocomposite will be reduced to a few Siemens/meter (S/m).

In some embodiments the polymer is Polydimethylsiloxane (PDMS). Additional polymers may include, for example, Poly(methyl methacrylate) (PMMA), Polyurethane (PUR and PU), Polystyrene (PS), Ethylene Copolymer, Cyclo Olefinecopolymer, Cyclic Olefin Polymer (COC), Ethylene-norbomene Copolymer, Low Density Polyethylene (LDPE), High Density Polyethylene (HDPE), Polypropylene (PP), Polyvinyl Chloride (PVC), Nylon, Teflon (Polytetrafluoroethylene), Thermoplastic polyurethanes (TPU), ethylenedioxythiophene silicones, Polyethylene poly (styrenesulfonate), polycarbazoles, polyindoles, and polyazepines.

In some embodiments the metal nanoparticles may include, but are not limited to, metals such as nickel, silver, gold, copper, palladium, ruthernium or iron.

Some embodiments of the present invention include a novel and simplified method of producing the nanoparticle-polymer nanocomposite. The previous portions of the application describe a method of fabricating highly adhesive and uniform morphologically transformed nanostructures (MTNS) on the surface of polymer films. In some embodiments of the invention, as described above, the formation of MTNS structures is achieved by the reduction of metal salts and high temperature annealing. The annealing is used to segregate the metal nanoclusters formed on the surface of the polymer and hence in some embodiments the optical properties of the nanocomposite are enhanced for use in biosensing applications. The nanocomposite that is produced as described below is compatible to produce micro and/or nano features using various micromolding or nanomolding techniques.

In some embodiments, fabrication of the nanocomposite is simplified by reducing the metallic (for example gold or silver) nanoparticles (NPs) in the polymer base during preparation of the polymer followed by the addition of dry conducting nanoparticles of different sizes and/or shapes, which allows for further tenability of the conductivity of the polymer. Examples of dry conducting nanoparticles may include carbon nanotubes, metal nano-rods and/or spherical nanoparticles. Nanoparticles are being referred to as particles having one or more dimensions of the order of 200 nm or less and can have different geometric and random shapes, for example, but not limited to, chips, flakes, wires, rods, spheres, hexagons, stars, etc.

In some embodiments, the nanocomposite polymer is fabricated based on a partial reduction of metal salts, which balances the reduction of nanoparticles and the crosslinking of the polymer. In some embodiments, the partial reduction of metal salts is achieved by a controlled addition of curing agent and solvents of metal salts. This reduction process does not limit the distribution of nanoparticles on only the surface of the PDMS, but uniformly distributes the nanoparticles over the entire polymer matrix. Moreover, in some embodiments, the morphology transformation of the MTNS by a high temperature annealing is not performed. The process of adding the curing agent and the solvents having the corresponding metal salts is controlled to form the nanocomposite of the polymer having uniformly distributed NPs.

The electrical conductivity of the nanocomposite in some implementations may be low, therefore the addition of high aspect ratio conductive nanoparticles via mechanical stimulation may be used to increase the conductivity of the nanocomposite. The stimulation provides thorough mixing of the high aspect ratio conductive nanoparticles throughout the matrix of the polymer and to make conductive bridges between in-situ syntheized particles. Therefore, different shapes and sizes of externally added nanofeatures will facilitate the effective conductive bridging of nano-composite. The electrical conductivity can be tuned via changing the partial reduction of metal salts in the crosslinking agent, which in terms of creating the polymer is to be considered in some embodiments the curing agent or by changing the weight/volume percentage of the high aspect ratio conductive nanoparticles. The electrical conductivity of nano-integrated functional nanocomposite polymers fabricated according to embodiments of the invention can be tuned from $6.3694 \times 10^{5+5}$ S/m to $1.5625 \times 10^{-3}$ S/m. The concentration of nanoparticles required for insulator to conductor transition also referred to as threshold concentration or percolation limit can vary from 0.01 to 85-weight percentage depending on the type, shape, size, morphology and elemental composition of nanoparticles.

The percentage of nano features produced through reduction and mechanical stimulation will differ based on the application and conductivity required. The process of mechanical stimulation may include, but is not limited to, centrifuge mixing, ultrasonic mixing, acoustic mixing, laser based mixing, mechanical stirring.

In some embodiments, the formation of MTNS structures is enabled without having to perform high temperature annealing.

In some embodiments, the invention provides a method of fabricating the polymer based nanocomposite having metal nanoparticles uniformly distributed over the entire matrix of the polymer without limiting the distribution of nanoparticles to only the surface of the polymer.

In some embodiments, the invention is suitable for fabrication of micro devices that include a metal nanoparticle reinforced polymer with optical, chemical, mechanical, electrical and thermal properties, of which some or all can be tuned to the desired values.

A nanocomposite material produced as described herein through a combination of in-situ reduction and mechanical stimulation can be used when forming micro or nano structures.

In a particular non-limiting example in which the nanoparticle nanocomposite polymer that was synthesized was silver-PDMS-multiwalled carbon nanotube nanocomposite, the conductivity was calculated to be $1.2 \times 10^{-2}$ S/m, wherein the weight percentage of multiwalled carbon nanotubes in the in-situ-reduced Silver Nitrite and PDMS composite was 0.5%.

In some embodiments, formulations containing carbon nanoparticles or their derivatives, such as grapheme or carbon nanotubes, show a negative temperature coefficient of resistivity (NTCR).

In some embodiments, formulations of the nanocomposite containing terfinol-d, gerfinol and their derivatives can be remotely actuated using radio frequencies (RF). This may be particularly useful in applications such as, for example, energy scavenging, RF antennas, and RF communications.

In some embodiments, formulations of the nanocomposite containing hard magnetic materials can be remotely actuated by magnetic fields. In some embodiments, formulations of the nanocomposite containing hard magnetic materials can be used to fabricate resettable hard magnets can be made.

The following is an example of how a particular Gold-PDMS nanocomposite material may be fabricated.

The preparation of the example nanocomposite starts with mixing of a PDMS base and a crosslinking agent in 4:1 ratio. In this example, Gold (III) chloride trihydrate ($HAuCL_4.3H_2O$) is dissolved in de-ionized (DI) water or ethanol, resulting in a solution of 5% Gold in the DI water or ethanol, which is used for the preparation of the nanocomposite. The concentration of metal salt, Gold (III) chloride trihydrate in this case, can be adjusted depending upon the particular application of the nanocomposite. The ethanol or DI water having the Gold (III) chloride trihydrate is added to the combined mixture of the PDMS base and curing agent in a 1:1 ratio that results in a PDMS-NP mixture. The color of PDMS-NP mixture may slowly change to a purple colour over several minutes, which indicates the reduction of the salt to the metal nanoparticle. The PDMS-NP mixture is degassed to remove gas bubbles in the mixture. Then, the dry conducting nanoparticles of different sizes and/or shapes are mixed with the PDMS-NP mixture through mechanical stimulation to allow tenability of the conductivity of the eventual nanocomposite polymer The PDMS-NP mixture together with dry conducting nanoparticles can be spin coated and baked at approximately 100° C. for 5 hours. The wt % of the metal particle can be increased or decreased to any desired wt % by increasing or decreasing the concentration of Gold (III) chloride trihydrate in the ethanol or DI water to tune the electrical properties of the nanocomposite for different electrical applications.

Figure 21:
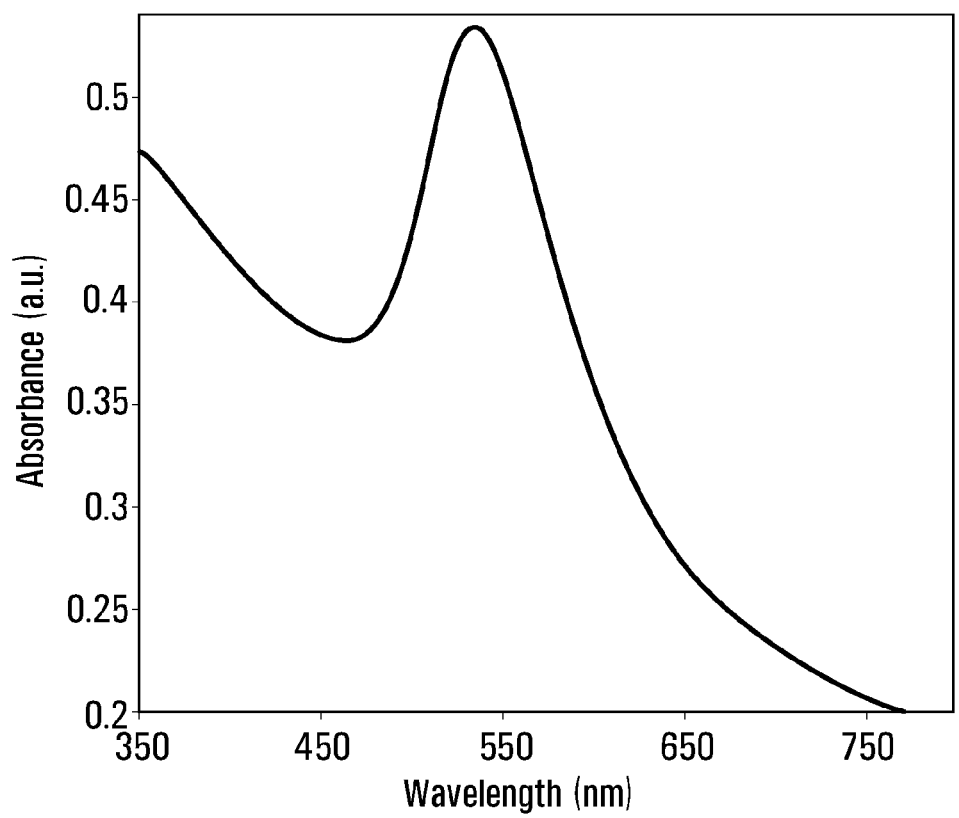
FIG. 21 is a graphical plot illustrating UV-VIS absorbance spectrum of the gold-PDMS nanocomposite.

FIG. 21 is a plot of wavelength in nanometers (nm) versus absorbance (a.u) for an example nanocomposite of gold nanoparticles fabricated according to an embodiment of the invention. The optical absorbance spectrum was measured in the UV-Visible region (350 nm to 750 nm) and an absorbance peak was found at approximately 535 nn for the band of gold nanoparticles.

In an alternative example fabrication for generating a Silver-PDMS nanocomposite, silver nitrate is dissolved in de-ionized (DI) water or ethanol and used to mix with the PDMS base and curing agent and dry conducting nanoparticles. In a particular implementation of the invention that was synthesized, the electrical conductivity of the nanocomposite was determined to be as high as $6.3694 \times 10^5$ S/m with the addition of high aspect ratio conducting nanoparticles (carbon nanotubes) via mechanical stimulation. The wt % of the carbon nanotubes and silver in the polymer was 2% and 20%.

Figure 24:
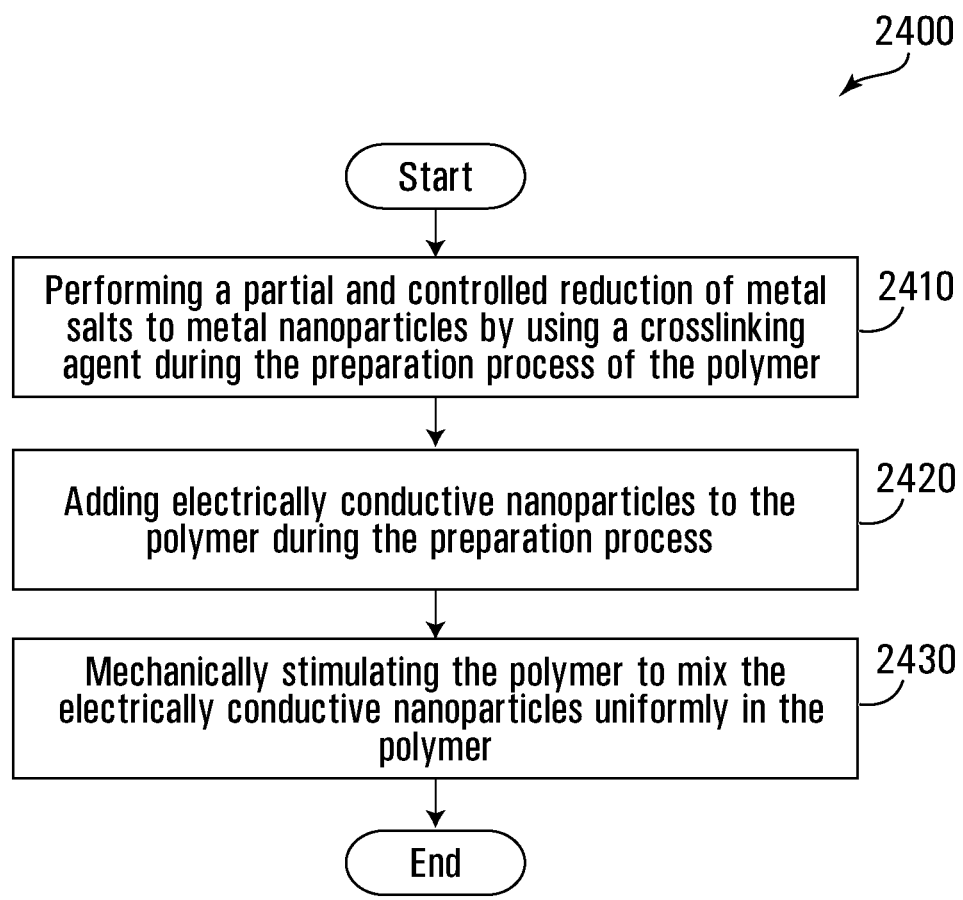
FIG. 24 is a flow chart of a method for fabricating a metallic nanocomposite material according to embodiments of the invention.

FIG. 24 is a flow chart describing a method 2400 according to an aspect of the invention for fabrication of nanoparticle reinforced polymer. A first step 2410 includes performing a partial and controlled reduction of metal salts to metal nanoparticles by using a crosslinking agent during the preparation process of the polymer. A second step 2420 then includes adding electrically conductive nanoparticles to the polymer during the preparation process. A third step includes mechanically stimulating the polymer to mix the electrically conductive nanoparticles uniformily in the polymer.

In some embodiments, performing a partial and controlled reduction of metal salts to nanoparticles enables tuning at least one of optical, electrical, mechanical, thermal and chemical properties of the polymer for various applications by controlling the percentage weight (wt %) of the nanoparticles in the polymer by adjusting an amount of curing agent and a concentration of the metal salts during preparation of polymer.

In some embodiments the tuned optical properties and surface properties of the nanoparticle reinforced polymer aid in immobilizing bio/chemical test material for easier detection by virtue of the uniform distribution of nanoparticles on the surface of nanocomposite. For example, detection performed by measuring the localized surface plasmon resonance.

While the main polymer discussed in the examples above is indicated to be PDMS, it is to be understood that alternative polymers could be used in manufacturing the nanoparticle reinforced polymer such as those discussed above.

In some embodiments the nanocomposite is used for microelectronic and/or electronic sensors and applications. In some embodiments the nanocomposite may be used to form part of any component that is flexible like beams, cantilevers, plates, diaphragms, actuators, etc. that are moving or stationary.

The process described herein is suitable for applications where high conductivity and advantages of PDMS may be beneficial.

Nanocomposite fabricated by processes described herein may be used to make nano-integrated sensor systems for various applications, such as, but not limited to, the following areas: bio-potential measurements, bioMEMS, Nano-integrated-MEMS, tunable antennas, flexible electronics, tactile sensors etc.

The nanocomposite can be nano and/or micro-patterned using techniques, such as, but not limited to, screen printing, molding, nano-micro-contact printing, laser machining, stereolithography, nanoimprint lithography, double-patterning and magnetolithography.

Nano-microscale printing of the developed nanocomposite can be done on various dielectric and non-dielectric substrates, non-limiting examples include: fabrics, plastics, and glass.

In some embodiments, fabrication of the nanoparticle polymer nanocomposite may involve in-situ and mechanical stimulation synthesis of chlorinated-silver-nitrite and silver powder for use in water based screen printing to form silver-chloride bio-potential electrodes for biomedical applications and wearable garments. The nanocomposite is patternable for fabricating flexible polymer sheets suitable for making smart garments with integrated sensor arrays of nanoelectrodes than can be used for bio-impedance imaging. Potential applications of such smart garment may include detection of breast, brain and skin cancers and monitoring the process of treatment.

The following is a list of specifications of the nanocomposite fabricated according to some embodiments of the invention:

Optical absorbance peak at 535 nm useful for the optical detection of biological species without the mechanical stimulation of nanoparticles;

With the addition of carbon nanotubes and silver nanoparticles, the electrical resistivity tunability range: $1.57 \times 10^{-6}$ $\Omega$-m to $6.40 \times 10^2$ $\Omega$-m;

Operating temperature range for enclosed environments: −100 to 400° C. (tested under lab conditions);

Operating temperature range for open environments: −100 to 600° C. (tested under lab conditions);

Negative Temperature Coefficient Resistance (NTCR)- resistivity decreases with increase in temperature, making it an ideal candidate for temperature sensors;

Stretch-ability: Retains electrical properties on being stretched, bent, flexed or twisted;

Micro-patternability using UV lithography, down to a feature size of 5 μm;

Micro-patternability using $CO_2$ Laser lithography, down to feature size of 25 μm;

Micro-patternability using Screen printing, Down to feature size of 50 μm;

Micro-contact printing down to feature size of 500 nm possible;

Stereo-lithography possible;

Inkjet printing possible;

Nano-patternability using nano-imprint lithography, down to 10 nm and above (dependent of nanoparticle size);

Electrospinning nanofibers possible;

Large scale fabrication on 42 inch×42 inch substrates possible;

Substrates on which nanocomposite can be printed include metals, glass, plastics, and fabrics;

Can conform to any geometrical shape: curved, sharp edge, oval, spherical and rectangular, dented; and Integration of discrete electronic components such as IC's, and other conventional electronic devices and sensors possible.

In some embodiments, devices such as micro-heaters, micro-temperature sensors, flexible electronics and flexible antennas can be fabricated using the nanocomposite material. The nanocomposite material can be used for devices that can be used for signal routing (flexible printed circuit boards (PCB)) and electromagnetic interference (EMI) shielding. The nanocomposite material can be used for fabricating flexible shape conforming printed circuit boards and electrostatic superhydrophobic coatings.

The nanocomposite can be used as replacement for copper wires as the weight of some nanocomposite materials fabricated according to some embodiments of the invention are approximately ¼ the weight of copper.

The process according to aspects of the invention is suitable for electrical applications where high conductivity and advantages of polymer, such as for example, PDMS are beneficial.

The nanocomposite when synthesized to have a higher conductivity can be used for various microelectronics and/or electronic sensors. The nanocomposite when synthesized to have enhanced mechanical properties can be used for mechanical sensors and/or actuators, such as micro-cantilevers.

Nanocomposite can be used to make nano-integrated sensor systems for various applications but not limited to following areas: bio-potential measurements, bioMEMS, Nano-integrated-MEMS, tunable antennas, flexible electronics, tactile sensors etc.

The nanocomposite can be nano-micropatterned via, but not limited to, screen printing, molding, nano-micro-contact printing, laser machining, stereolithography, nanoimprint lithography, double-patterning and magnetolithography. Nano-microscale printing of the developed nanocomposite can be performed on various dielectric and non-dielectric substrates, non-limiting examples of which include: fabrics, plastics, and glass.

The nanocomposite is tunable shape conformable and micro/nano patternable for various electrical signal routing applications. The nanocomposite is suitable and tunable for various heating applications. The nanocomposite is suitable for various sensing applications including, biological, thermal and mechanical sensing. The nanocomposite is suitable for the biological sensing via micro and nano electro-mechanical transduction. The nanocomposite is suitable for the thermal sensing with its unique thermo-electric properties. The nanocomposite is suitable for various mechanical sensing including stresses, strain, tactile, and force sensing with its unique tunable electro-mechanical properties.

The nanocomposite may have numerous applications in aerospace industries because of the shape conformability, micro-nano patternability and unique thermo-electric, electro-mechanical properties. For example, the nanocomposite is suitable for fabricating micro-heating elements and integrating with the aerofoil.

The nanocomposite is suitable for electromagnetic interference (EMI) shielding of device having any shape due to the unique moldability, shape conformability and higher electrical conductivity.

The nanocomposite is suitable non-destructive testing, health monitoring and imaging of aircraft parts such as aerofoils, engines, blades structure. The imaging may aid in crack detection, stress level testing and deformation of the materials. when under stress.

The nanocomposite fabricated according to some embodiments of the invention can be used to fabricate on-garment ECG, EKG, and bio-potential sensors for health monitoring of the human body, especially for flight crew, astronauts, military etc.

Figure 22:
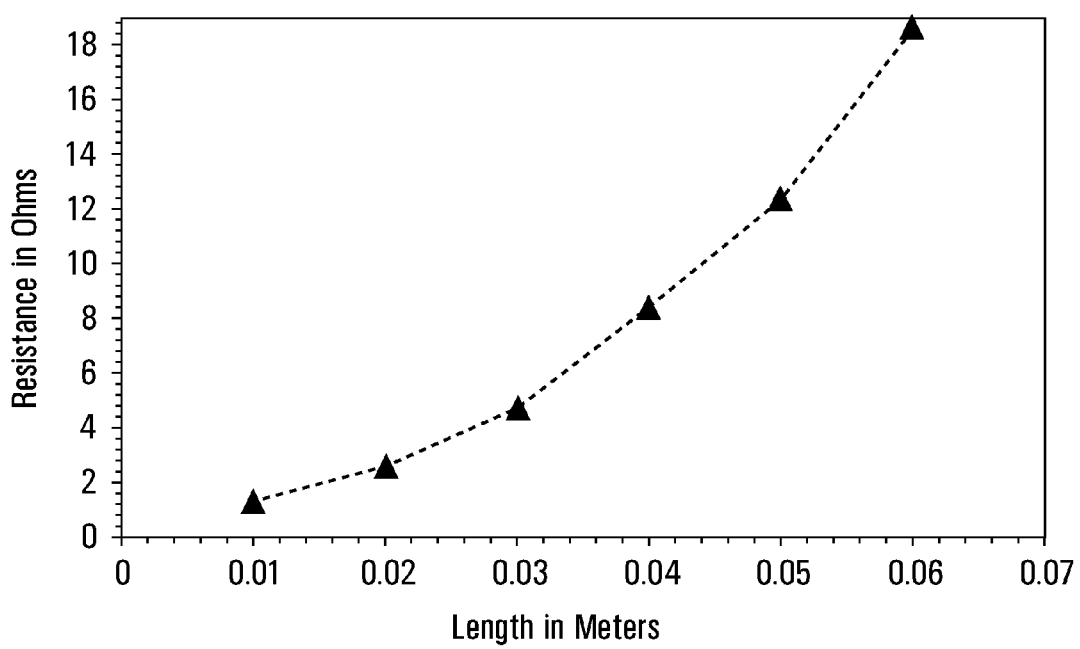
FIG. 22 is a graphical plot of electrical resistance measured versus the length of a nanocomposite material fabricated according to an embodiment of the invention.

FIG. 22 is plot of length in meters (x-axis) versus electrical resistance (y-axis) of an examplary nanocomposite fabricated according to an embodiment of the application measured in ohms. The nanocomposite was fabricated using the combined process of in-situ reduction of gold on PDMS and mechanical stimulation of silver nanoparticles and carbon nanotubes.

The resistance was measured in cross-section of $3.2 \times 10^{-3}$ $m^2$. The nanocomposite material in this example was annealed at 200° C. after curing the polyer base of the nanocomposite.

Other potential applications may include patterning the nanocomposite material for various applications such as electrical signal routing, heating pads with ribbon cables that can be integrated with aerofoils, strain gauges and interdigitated electrodes.

Joule heating, also known as ohmic heating and resistive heating, is the process by which the passage of an electric current through a conductor releases heat. The properties of the developed nanocomposite can be tuned to adjust to any specific application where such heating may be desirable.

Figure 23:
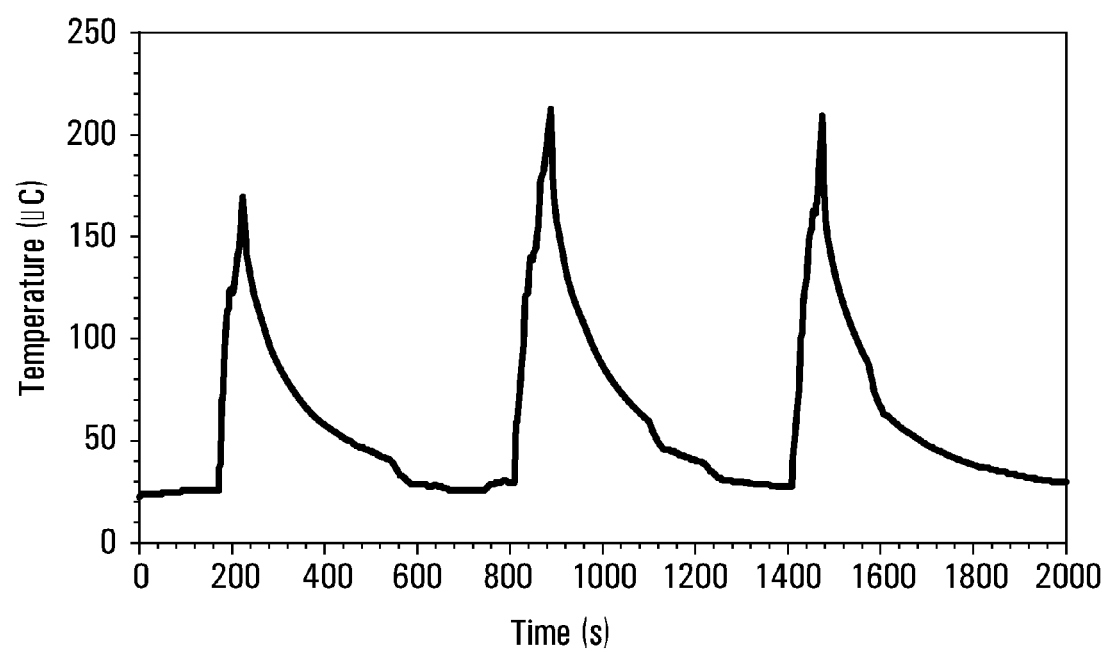
FIG. 23 is a graphical plot of a heating-cooling cycle of a nanocomposite material fabricated according to an embodiment of the invention.

FIG. 23 is a plot of a heating-cooling cycle of a typical nanocomposite. Time in seconds (s) is plotted on the x-axis and temperature in degrees Celsius (° C.) is plotted on the y-axis. The resistance of the particular nanocomposite material that was experiments on was 1 ohm (resistivity of $1.57 \times 10^{-6}$ $\Omega$-m), the voltage applied was 5 volts and the current measured was 3 A. By applying the particular voltage, the temperature of the nanocomposite can be seen to vary from ambient temperature of approximately 23° C. to between 170° C. and 210° C. The temperature rise occurred over approximately 60 seconds and the fall over approximately 400 seconds.

As the nanocomposite has the properties described above of being light, flexible and patternable, it may be possible to fabricate a patterned nanocomposite that includes heating pads with ribbon cables that can be integrated with aerofoils to aid in de-icing airplane wings and mitigate ice build-up.

Numerous modifications and variations of the present invention are possible in light of the above teachings. It is therefore to be understood that within the scope of the appended claims, the invention may be practiced otherwise than as specifically described herein.

The invention claimed is:

1. A method of fabrication of a nanoparticle reinforced polymer comprising:

performing a partial and controlled reduction of metal salts to metal nanoparticles by using a crosslinking or curing agent during a preparation process of a polymer base; and adding electrically conductive nanoparticles to the polymer base during the preparation process, wherein the partial reduction and the adding electrically conductive nanoparticles occurs when the polymer base is in a liquid state before the polymer base cures to a solid state.

2. The method of claim 1 wherein performing a partial and controlled reduction of metal salts comprises controlling the reduction by varying a concentration of the metal salts and the crosslinking agent.

3. The method of claim 1, wherein performing a partial and controlled reduction of metal salts to metal nanoparticles comprises:
tuning at least one of optical, electrical, mechanical, thermal and chemical properties of the polymer base for various applications by controlling the percentage weight (wt %) of the metal nanoparticles in the polymer by adjusting an amount of crosslinking agent and a concentration of the metal salts during preparation of polymer base.

4. The method of claim 3, wherein the tuned at least one of optical, electrical, mechanical, thermal and chemical properties of the nanoparticle reinforced polymer aid in immobilizing bio-chemical test material for easier detection by virtue of uniform distribution of nanoparticles on a surface of the nanoparticle reinforced polymer.

5. The method of claim 1, wherein subsequent to adding the electrically conductive nanoparticles to the polymer base, the method further comprises mechanically stimulating the polymer base to mix the electrically conductive nanoparticles, having same or different shapes and sizes, uniformly in the polymer base.

6. The method of claim 1, wherein the polymer base is a material selected from the group consisting of: Polydimethylsiloxane (PDMS); Poly(methyl methacrylate) (PMMA); Polyurethane (PUR and PU); Polystyrene (PS); Ethylene Copolymer; Cyclo Olefinecopolymer; Cyclic Olefin Polymer (COC); Ethylene-norbomene Copolymer; Low Density Polyethylene (LDPE); High Density Polyethylene (HDPE); Polypropylene (PP); Polyvinyl Chloride (PVC); Nylon; Teflon (Polytetrafluoroethylene); Thermoplastic polyurethanes (TPU); ethylenedioxythiophene silicones; Polyethylene poly(styrenesulfonate); polycarbazoles; polyindoles; and polyazepines.

7. The method of claim 1 further comprising using the nanoparticle reinforced polymer for fabricating microdevices and nanodevices having nanostructures with enhanced material properties.

8. The method of claim 1 further comprising using the nanoparticle reinforced polymer for fabricating flexible micro or nano electronics or electrical circuits.

* * * * *